US012396719B2

(12) United States Patent
Hart et al.

(10) Patent No.: US 12,396,719 B2
(45) Date of Patent: Aug. 26, 2025

(54) SOFT TISSUE FIXATION SYSTEM

(71) Applicant: EndoFix Medical Technologies, Inc., Plainville, MA (US)

(72) Inventors: Rickey Hart, Wrentham, MA (US); Peter Rogal, Rochester, VT (US)

(73) Assignee: EndoFix Medical Technologies, Inc., Plainville, MA (US)

( * ) Notice: Subject to any disclaimer, the term of this patent is extended or adjusted under 35 U.S.C. 154(b) by 316 days.

(21) Appl. No.: 18/120,801

(22) Filed: Mar. 13, 2023

(65) Prior Publication Data

US 2023/0285015 A1 Sep. 14, 2023

Related U.S. Application Data

(60) Provisional application No. 63/319,467, filed on Mar. 14, 2022.

(51) Int. Cl.
*A61B 17/04* (2006.01)
(52) U.S. Cl.
CPC .. *A61B 17/0401* (2013.01); *A61B 2017/0409* (2013.01); *A61B 2017/0464* (2013.01)
(58) Field of Classification Search
CPC ........ A61B 17/0401; A61B 2017/0409; A61B 2017/0464; A61B 17/0466; A61B 2017/06052; A61B 2017/0406; A61B 2017/0458
See application file for complete search history.

(56) References Cited

U.S. PATENT DOCUMENTS

| | | | |
|---|---|---|---|
| 8,303,604 B2 | 11/2012 | Stone et al. | |
| 9,622,738 B2 | 4/2017 | Dreyfuss et al. | |
| 9,713,464 B2* | 7/2017 | Overes | A61B 17/0401 |
| 9,737,292 B2 | 8/2017 | Sullivan et al. | |
| 9,974,534 B2 | 5/2018 | Troxel et al. | |
| 10,016,192 B2 | 7/2018 | Beck | |
| 10,799,231 B2 | 10/2020 | Best et al. | |
| 11,006,944 B2 | 5/2021 | Best et al. | |
| 11,154,292 B2 | 10/2021 | Meister et al. | |

(Continued)

OTHER PUBLICATIONS

International Search Report for International Application No. PCT/US2023/015126, mailed Jul. 5, 2023, 10 pages.

*Primary Examiner* — Julian W Woo
(74) *Attorney, Agent, or Firm* — Nutter McClennen & Fish LLP

(57) ABSTRACT

A single delivery needle configuration accommodates multiple soft tissue fixation devices at once. The configuration eliminates the need to reload a fixation delivery device when multiple fixation devices are required. Further, this configuration can include different variations of fixation devices. In embodiments, these fixation devices are typically manufactured from standard braided polyester suture that is cut into segments with predetermined lengths. This design allows the braided suture segments to be preloaded with a suture threaded through the preloaded braided suture segments with a slip knot placed on the proximal end of a first braided suture segments (e.g., distal fixation device). The tailing suture from the slip knot passes through the second, third, fourth braided suture segments, or any required quantity of braided suture segments that have been preloaded into the delivery device. The suture passes completely through a delivery device.

16 Claims, 20 Drawing Sheets

(56) References Cited

U.S. PATENT DOCUMENTS

| | | | |
|---|---|---|---|
| 11,666,320 B2* | 6/2023 | Johnson | A61B 17/0401 |
| | | | 606/232 |
| 2019/0150909 A1 | 5/2019 | Stone et al. | |
| 2023/0056585 A1 | 2/2023 | Goncalves | |
| 2023/0285015 A1* | 9/2023 | Hart | A61B 17/0466 |

* cited by examiner

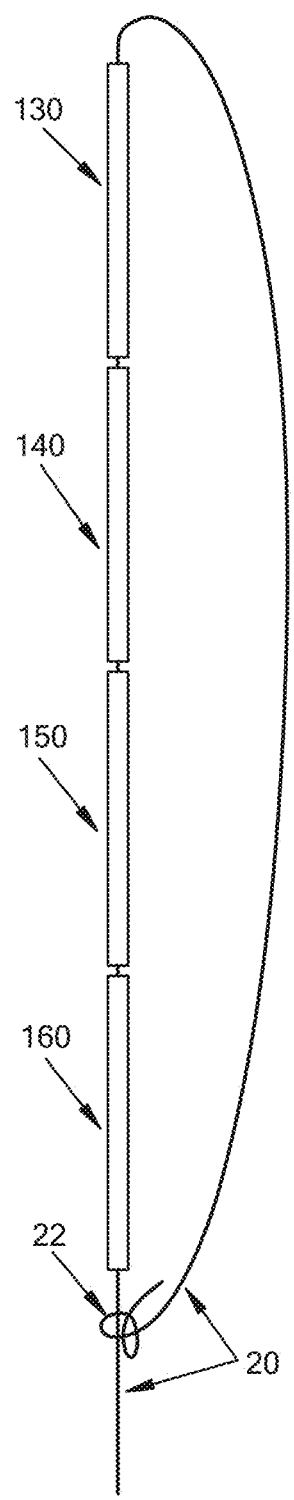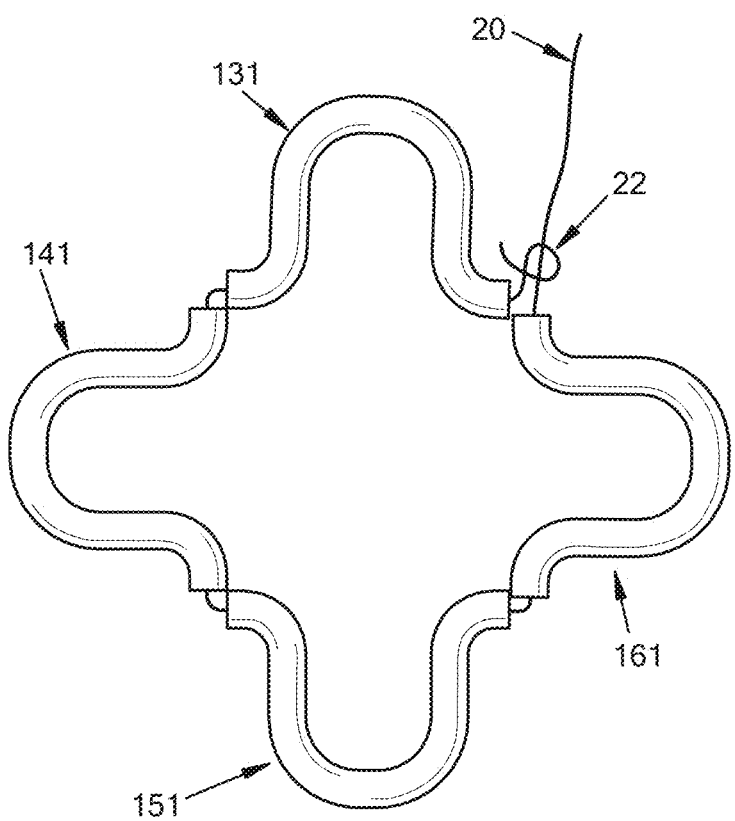
FIG. 6A
FIG. 6B

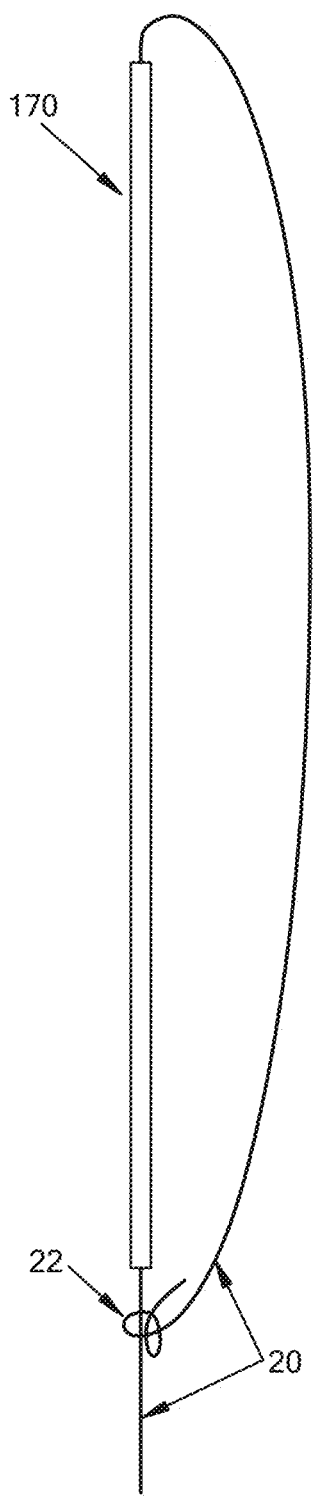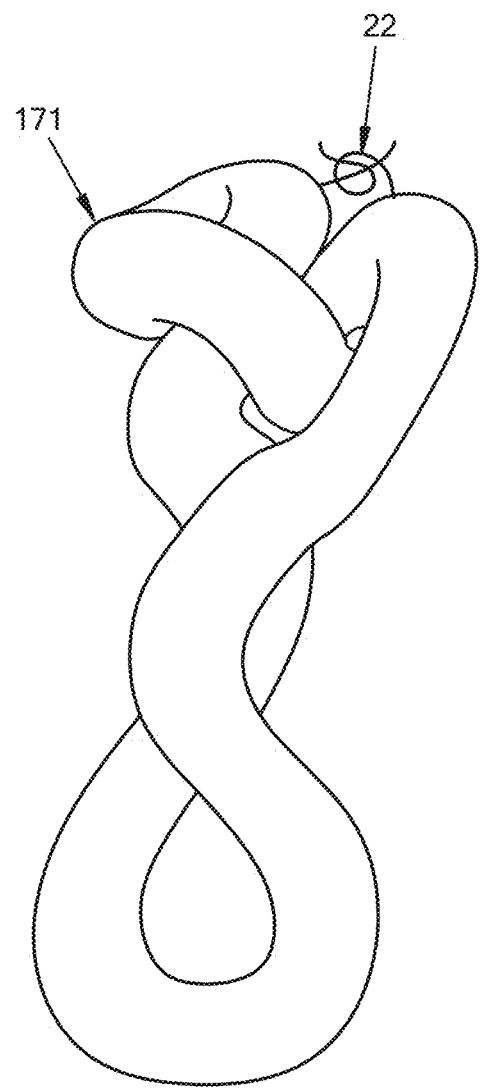
FIG. 7A
FIG. 7B

SOFT TISSUE FIXATION SYSTEM

PRIORITY

This patent application claims priority from provisional U.S. patent application No. 63/319,467, filed Mar. 14, 2022, entitled, "SOFT TISSUE FIXATION SYSTEM," and naming Rickey Hart, Brian Tinkham, and Peter Rogal as inventors, the disclosure of which is incorporated herein, in its entirety, by reference.

FIELD

Illustrative embodiments of the invention generally relate to surgical tissue fixation and, more particularly, various embodiments of the invention relate to devices and methods of deploying the devices to fixate tissue.

BACKGROUND

Surgical Fixation devices have primarily been manufactured from stainless, titanium, non-absorbable plastic, absorbable plastic or some hybrid of plastic and ceramic. However, the use of flexible fixation devices is far less common.

There is a particular need in medical treatment settings of fixating soft tissues, such as closing gastroenterological defects, and for that matter devices that could be used for any soft tissue to tissue approximation.

SUMMARY OF VARIOUS EMBODIMENTS

In accordance with one embodiment of the invention, a flexible braided anchor assembly for tissue fixation includes a flexible strand (e.g., suture), and a plurality of braided anchor segments slidably coupled to the flexible strand. The flexible strand passes through a bore hole that traverses from a proximal end to a distal end of each of the plurality of braided segments. The proximal end of a first braided anchor segment is adjacent to a distal end of the second braided anchor segment. The plurality of braided anchor segments are cinched together forming a flexible braided anchor assembly to provide tissue fixation.

The plurality of braided anchor segments may include straight braided suture segments that have been deformed by the application of tension on the flexible strand. The flexible strand may be a monofilament. The flexible strand may be a suture. The suture may be a braided polyester suture. Each of the plurality of braided anchor segments may be a standard braided polyester suture that is cut into predetermined lengths.

Each of the plurality of braided suture segments slidably coupled to the flexible strand may be treated to increase a rigidity of the plurality of braided suture segments slidably coupled to the flexible strand. Such a treatment may include heating each of the plurality of braided suture segments. Such a treatment may also include applying a cyanoacrylate coating to each of the plurality of braided suture segments.

The cinched plurality of braided anchor segments may have a purse string effect on the plurality of braided anchor segments such that the plurality of flexible braided anchor segments is gathered to provide tissue fixation.

In accordance with another embodiment of the invention, a method for implanting a plurality of braided suture segments connected via a single flexible strand for tissue fixation includes puncturing the tissue at a first location with a delivery needle and extruding a first braided suture segment from the delivery needle. The first braided suture segment is the first of a plurality of braided suture segments slidably coupled to a flexible strand. The flexible strand is threaded through a bore hole in the first braided suture segment.

The method further includes pulling the flexible strand a first time to deform the first braided suture segment forming the first braided anchor segment. Pulling the flexible strand the first time tightens a slipknot around a proximal end of the first braided suture segment, and tightening the slipknot is configured to anchor the first braided anchor segment to the tissue to prevent the first braided anchor segment from pulling thru the tissue.

The method further includes withdrawing the delivery needle from the tissue a first time, puncturing the tissue at a second location with the delivery needle, extruding a second braided suture segment from the delivery needle, and pulling the suture a second time to deform the second braided suture segment forming the second braided anchor segment.

The method further includes withdrawing the delivery needle from the tissue a second time and pulling the suture a third time. The pulled suture causes the second anchor segment to be moved toward the first braided anchor segment.

The method further includes securing the suture to keep the tissue fixated by the plurality of braided suture segments, and cutting the suture. The suture is cut a distance away from the proximal end of a final braided anchor segment of the plurality of the braided anchor segments.

Following pulling the suture a third time, and before securing the suture, the method may further include puncturing the tissue at a third location with the delivery needle. The method may further include extruding a third braided suture segment from the delivery needle. The method may further include pulling the suture a fourth time to deform the third braided suture segment forming the third braided anchor segment. The method may further include withdrawing the delivery needle from the tissue a third time. The method may further include pulling the suture a fourth time, and the pulled suture may cause the third braided anchor segment to be moved toward the second braided anchor segment.

The first braided suture segment may be a primary first braided suture segment. Extruding the first braided suture segment may be accomplished by advancing first drive tube to push the first braided suture segment out of the delivery needle. After advancing the first drive tube to push the first braided suture segment out of the delivery needle, the first drive tube remains in an advanced position temporarily.

Extruding a second braided suture segment may be accomplished by advancing second drive tube to push the second braided suture segment out of the delivery needle. The second location may be between about 5 mm and about 20 mm from the first location.

Securing the suture may include a locking device or an overhead knot that can be run down to the fixation site. Securing the suture may include locking the suture in place using a locking mechanism comprising at least one of a tag, a barb, a cinch, a toggled needle, or a distal knot In accordance with yet another embodiment of the invention, a surgical device for implanting a flexible braided anchor assembly for tissue fixation includes a handle assembly. The handle assembly has a cylindrical bore passing through the handle assembly on a center axis along a length of the handle assembly.

The surgical device further includes an outer tube positioned in the cylindrical bore of the handle assembly. The outer tube is hollow and has a common center line with the cylindrical bore of the handle assembly. The outer tube includes a delivery needle having a needle tip at a distal end of the outer tube. The needle tip is a sharp point on the delivery needle.

The surgical device further includes a plurality of braided suture segments slidably coupled to a flexible strand, the flexible strand being translationally threaded through plurality of braided suture segments.

The surgical device further includes a first drive tube positioned in the outer tube and having a common center line with the outer tube. The first drive tube is configured to extrude a first braided suture segment.

The surgical device further includes a second drive tube positioned in the first drive tube and having a common center line with the first drive tube. The second drive tube is configured to extrude the remaining braided suture segments of the plurality of braided suture segments. The remaining braided suture segments of the plurality of braided suture segments are translationally threaded through and pressure fit within the first drive tube. Each of the plurality of braided suture segments may have a hollow braided suture segment.

The suture may be a monofilament strand. The plurality of braided suture segments may include a plurality of hollow braided suture segments aligned end to end having the monofilament strand threaded through the aligned plurality of hollow braided suture segments.

A column strength of the plurality of hollow braided suture segments may be increased by application of at least one of heat or a cyanoacrylate coating to each of the segments of the plurality of hollow braided suture segments.

A braided suture segment of the plurality of braided suture segments may have a length of between about 5 mm and about 50 mm. The braided suture segment of the plurality of braided suture segments may have a length of between about 5 mm and about 12 mm.

A distal end of the flexible strand threaded through the first braided suture segment may be looped around the first braided suture segment and knotted around the flexible strand between the first braided suture segment and the first drive tube.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 6A shows yet another embodiment of a braided suture segment.

FIG. 6B shows yet another embodiment of a braided suture segment.

FIG. 7A shows yet another embodiment of a braided suture segment.

FIG. 7B shows yet another embodiment of a braided suture segment.

DESCRIPTION OF ILLUSTRATIVE EMBODIMENTS

Figure 1A:
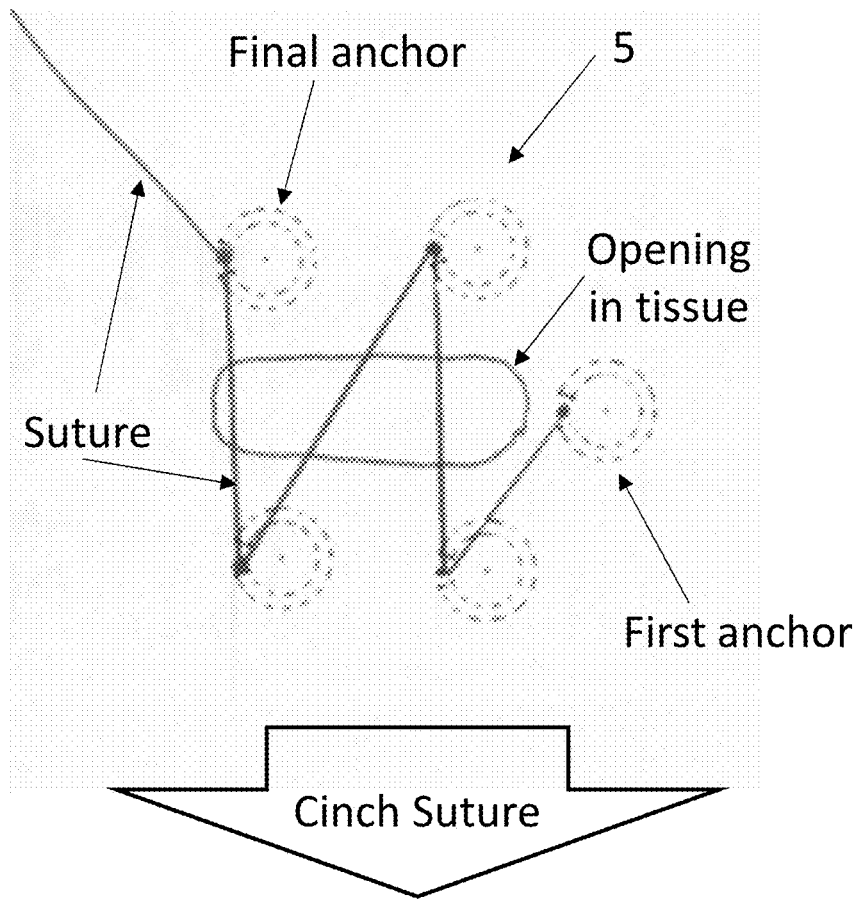
FIG. 1A shows a schematic plan view of a flexible braided anchor assembly for tissue fixation according to one embodiment of the present disclosure before cinching the suture tight.

The present disclosure includes a single delivery needle configuration which can accompany multiple soft tissue fixation devices at once. The device addresses tissue to tissue fixation. The configuration eliminates the need to reload a fixation delivery device when multiple fixation devices are required. Further, this configuration can include different variations of devices via: length; diameter; connectivity; function; and deployment. In embodiments, these presently disclosed fixation devices are typically manufactured from standard braided polyester suture that is cut into predetermined lengths.

This design would be preloaded with either a monofilament or a braided type suture with a slip knot placed on the proximal end of the distal fixation device. The tailing suture from the slip knot will pass thru the second, third, fourth fixation devices, or any required quantity of fixation devices. The suture will then pass completely through the delivery device where it can be coiled and placed onto a card for storage. Details of illustrative embodiments are discussed below.

To deploy the fixation devices, a series of internal tubes are required. A needle tip would first pierce a tissue and the distal fixation device would be pushed out of the delivery needle via a first tube. This tube will then lock in place inside the handle mechanism and will have further movement and used to house the remaining fixation devices. The delivery needle is then removed from the tissue and reapproximated to pierce the tissue in another location, typically about 5 mm to about 20 mm away. Then the next fixation device in line will be pushed out of the delivery needle. The needle tip is removed and the process will repeat for as many fixation devices as are loaded into the fixed tube.

When all the fixation devices have been placed in the tissue, the suture outside of the of delivery handle is pulled taut which creates a purse string effect. Now the delivery device can be removed and a locking device (e.g., locking mechanism) such as a cinch or special knot can be pushed down to complete and lock the purse string effect. Additional locking mechanisms that may be used include a tag, a barb, a cinch, a toggled needle, or distal knot. The remaining suture is cut.

Alternately an additional fixation device, as described above can be added to the delivery instrument such as to act as a locking device.

The fixation devices are advanced or driven by a handle assembly that employs an internal metering function of the devices for the predetermined length of each fixation device. The handle assembly controls the delivery tubes and locks when required.

In some embodiments, the fixation devices are a string of several hollow braided suture segments placed end to end over a flexible strand (e.g., monofilament, or a braided suture). The string of braided suture segments are stored in a tube and extruded out of the needle for delivery. The string of braided suture segments on the flexible strand (e.g., suture) has a certain column strength that is determined by a given composition and characteristics of the braided suture segments and the flexible strand. The column strength of a given string of braided suture segments may be strengthened (e.g., stiffened) by treating the braided suture segments. Given braided suture segments may be strengthened by heating the braided suture segments. Given braided suture segments may also be strengthened by coating them with a cyanoacrylate coating.

The braided suture segments may be formed of soft materials such as yarns, fibers, filaments, strings, fibrils, strands, sutures, etc., or any combination of such materials. The soft materials may be synthetic or natural materials, or combinations of synthetic and natural materials, and may be bio-degradable or non-degradable within the scope of this disclosure. In one non-limiting embodiment, the soft anchor assembly 10 is made exclusively of soft, suture-based materials.

Figure 1B:
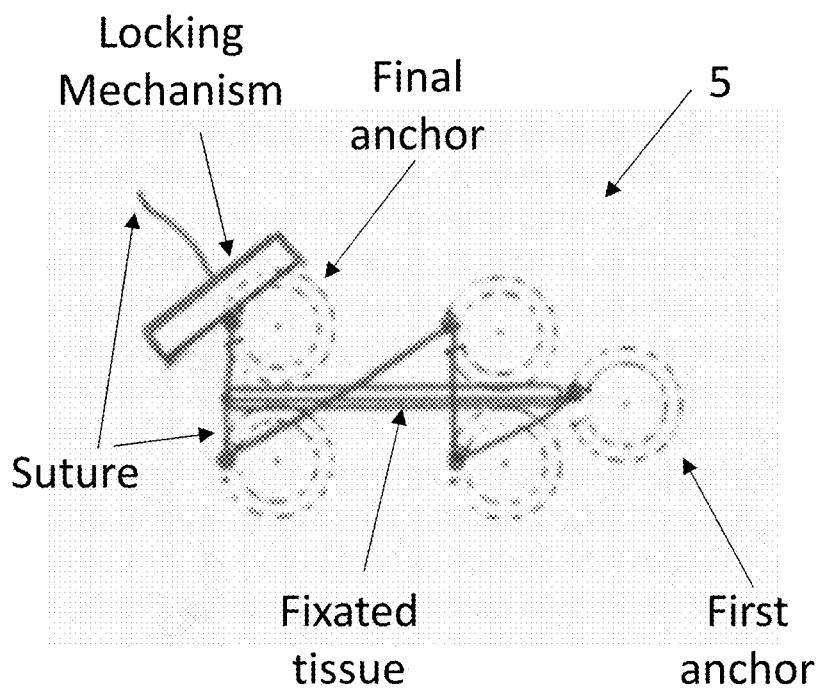
FIG. 1B shows a schematic plan view of a flexible braided anchor assembly for tissue fixation according to one embodiment of the present disclosure after cinching the suture tight.

FIG. 1A and FIG. 1B show schematic plan views of a flexible braided anchor assembly 5 for tissue fixation according to one embodiment of the present disclosure before and after cinching the suture tight. A suture (e.g., flexible strand) connecting the five anchor segments is shown on the proximal side (above the plane of the page) of the tissue. The five braided anchor segments are positioned on the distal side (below the plane of the page) of a tissue. The anchors are shown in dashed lines since the drawings are intended to show the anchors below the tissue surface.

In FIG. 1A, the flexible braided anchor assembly 5 includes anchors on one side (distal side) of a tissue that is to be repaired, and they are strung together on a suture that is displayed on the opposite side (proximal side) of the tissue. As shown in this embodiment, the five anchors are situated around an opening in the tissue that is to be repaired. The suture is anchored at the first braided anchor segment and connects anchor segments 2-5 with a single suture. The suture is free to extend beyond a final anchor.

In FIG. 1B, the flexible braided anchor assembly 5 has been drawn together to close and fixate the opening by pulling the suture taut. By pulling the suture taut, the exposed edges of the opening in the tissue are drawn together and the opening is fixated (e.g., joined). The opening has been closed by pulling the suture tight. A locking mechanism is engaged with the suture to lock the suture and prevent the fixated tissue from pulling apart. By tightening the suture to draw in the anchors and close the opening in the tissue, the flexible assembly of five braided anchor segments 5 has closed the opening like pulling purse strings to close a purse.

FIGS. 2A-2H show schematic cross section illustrations of some embodiments of delivery devices deploying an assembly of braided anchor segments.

Figure 2A:
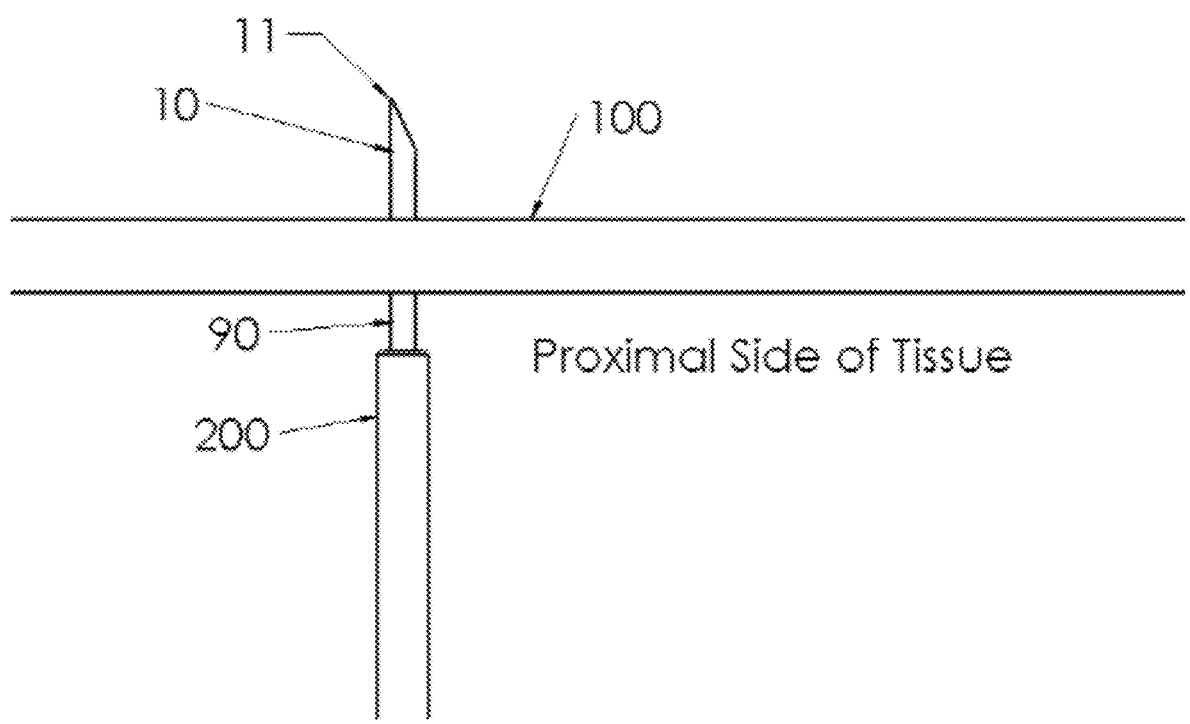
FIG. 2A shows a schematic cross section illustration of a delivery device with a needle after puncturing tissue according to an embodiment of the present disclosure.

FIG. 2A shows a schematic cross section illustration of a delivery device 15 with a needle 10 having a needle tip 11 after puncturing tissue 100 according to an embodiment of the present disclosure. The needle 10 punctures a first hole (not shown) in the tissue 100. The needle 10 punctures the tissue from a proximal side of the tissue 100 to a distal side of the tissue 100. The needle 10 is at a distal end of an outer tube 90, and the outer tube 90 is coupled to a handle assembly 200.

In some embodiments, the needle 10 and the outer tube 90 may be fabricated as a single piece, whereas in other embodiments, the needle 10 and the outer tube 90 may be assembled from separate pieces. The needle 10 and the outer tube 90 may be fabricated from one or more rigid materials, such as a steel, aluminum, titanium, and so on. The rigid material may also include metallic alloys such as nitinol. In embodiments, when the needle 10 and the outer tube 90 are assembled from separate pieces, the needle 10 and the outer tube 90 may be fabricated from different rigid materials.

Figure 2B:
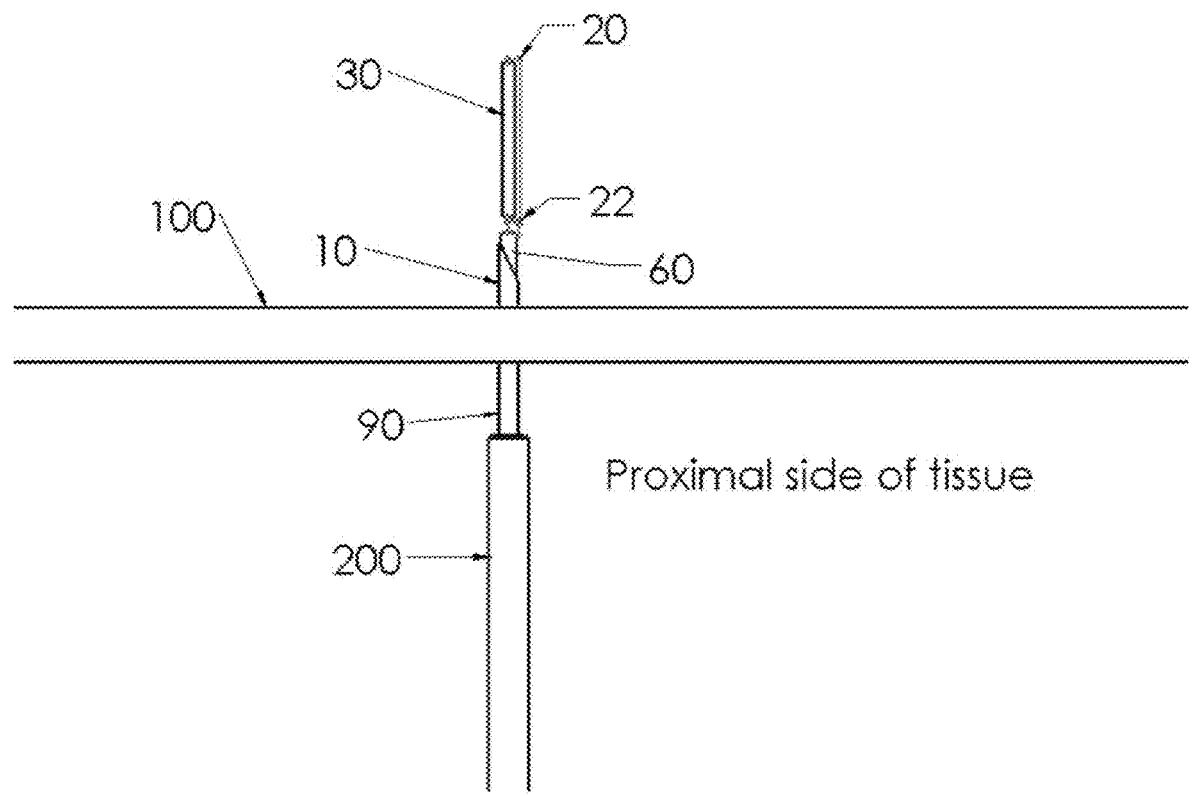
FIG. 2B shows a schematic cross section illustration of a delivery device with a first braided suture segment after being extruded from the needle on the distal side of the tissue.

FIG. 2B shows a schematic cross section illustration of a first braided suture segment 30 after being extruded from the needle 10 on the distal side of the tissue 100. The first braided suture segment 30 is pushout distally out of the needle by a first drive tube 60. A flexible strand (e.g., suture) 20 is shown threaded through the first braided suture segment 30, looped around, and knotted with a slidable slip knot 22 around the suture 20 between first braided suture segment 30 and the first drive tube 60.

In embodiments, the flexible strand (e.g., suture) 20 may be a monofilament. In other embodiments, the flexible strand 20 may be a suture. The suture 20 may be a braided polyester suture. In embodiments, the suture 20 may be a FiberWire®, TigerWire®, or FiberChain® suture, although any type of suture 20 may be utilized, including cored or coreless sutures. In another embodiment, the flexible strand 20 may be suture tape, such as FiberTape®. The flexible strand 20 may include any soft, flexible strand of material.

In some embodiments, the braided suture segments 30 may be strengthened by heating the braided suture segments 30. The braided suture segments may also be strengthened by coating them with a cyanoacrylate coating.

Figure 2C:
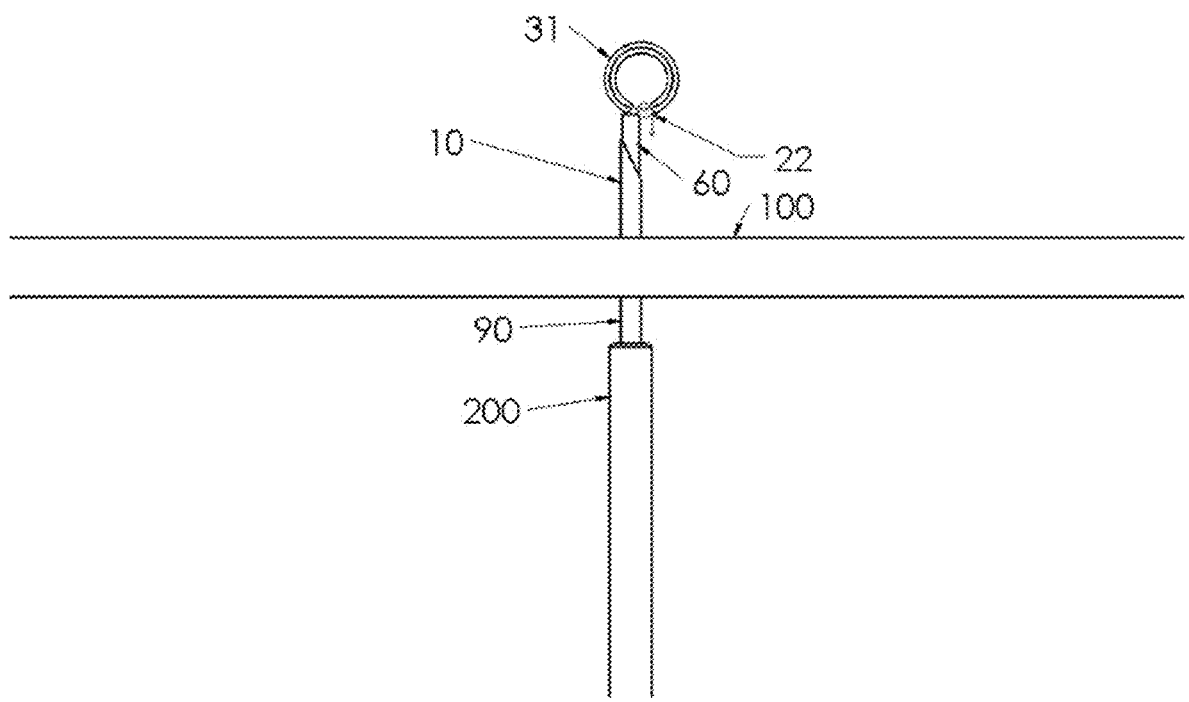
FIG. 2C shows a schematic cross section illustration of a delivery device with a first braided anchor segment after the suture has been pulled taut a first time.

FIG. 2C shows a schematic cross section illustration of a first braided anchor segment 31 after the suture 20 has been pulled taut a first time. As a result of the suture 20 being pulled tight, the first braided suture segment 30 has been deformed into a first braided anchor segment 31. The first braided suture segment 30 serves as an anchor to the flexible braided anchor assembly 5. By pulling the suture 20, the slip knot 22 is tightened to secure the first braided anchor segment on the distal surface of the tissue. The first braided anchor 31 may also be secured by locking the suture in place with any one of locking mechanisms including a tag, a barb, a cinch, a toggled needle, or a distel knot.

In embodiments where the braided suture segments have been strengthen by heating, or by coating them with a cyanoacrylate coating, deforming the braided suture segment by pulling suture 20 cracks or breaks up the coating on the braided suture segment 30.

Figure 2D:
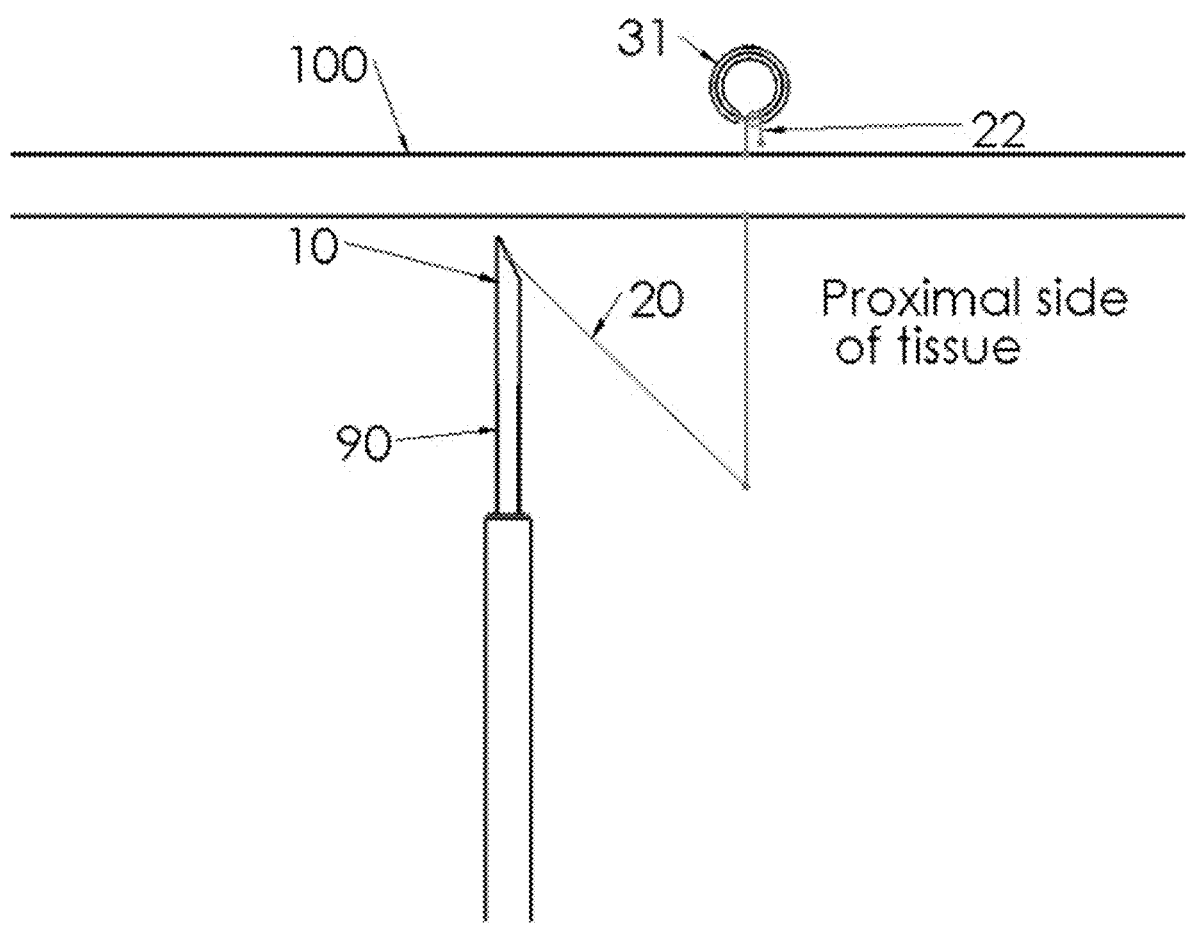
FIG. 2D shows a schematic cross section illustration of a delivery device with the needle being repositioned above the tissue prior to puncturing the tissue in a second location.

FIG. 2D shows a schematic cross section illustration of the needle 10 being repositioned above the tissue 100 prior to puncturing the tissue in a second location. In embodiments, the second location may be between about 3 mm and about 20 mm from the first location, whereas in other embodiments the second location may be between about 5 mm and about 15 mm from the second location, whereas in other embodiments the second location may be between about 8 mm and about 12 mm from the first location. After withdrawing the needle 10 from the tissue 100, there is approximately 4 cm of suture slack present prior to puncturing the tissue at the second location.

Figure 2E:
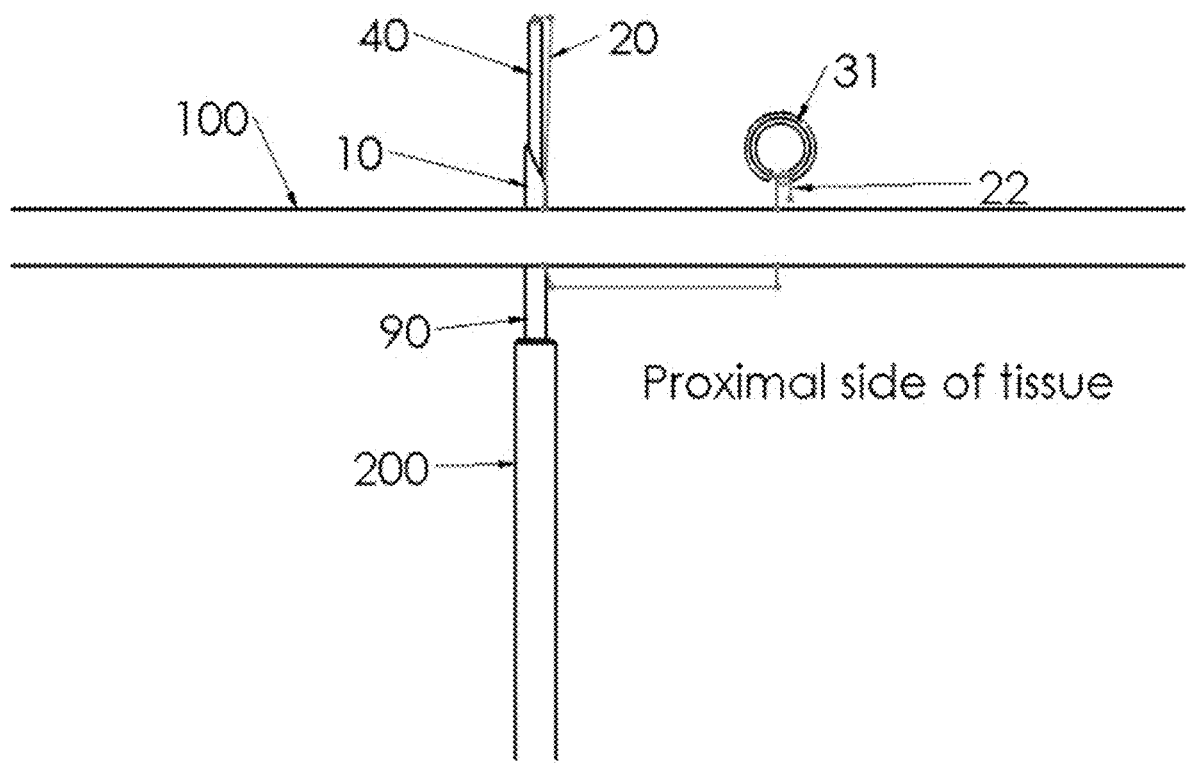
FIG. 2E shows a schematic cross section illustration of a delivery device with a second braided suture segment partially extruded from the needle.

FIG. 2E shows a schematic cross section illustration of a second braided suture segment 40 partially extruded from the needle 10. The second braided suture segment 40 is pushed from the needle by a second drive tube 70. The suture 20 passes from the first anchor segment 31 through the first hole (not shown), is strung along the proximal side of the tissue and is fed up through a second hole (not shown) made from puncturing the tissue a second time with the needle 10. The suture 20 loops around the second braided suture segment 40 and passes through a bore hole (not shown) in the second braided suture segment. The suture is threaded through the braided suture segments remaining in the outer tube 90.

Figure 2F:
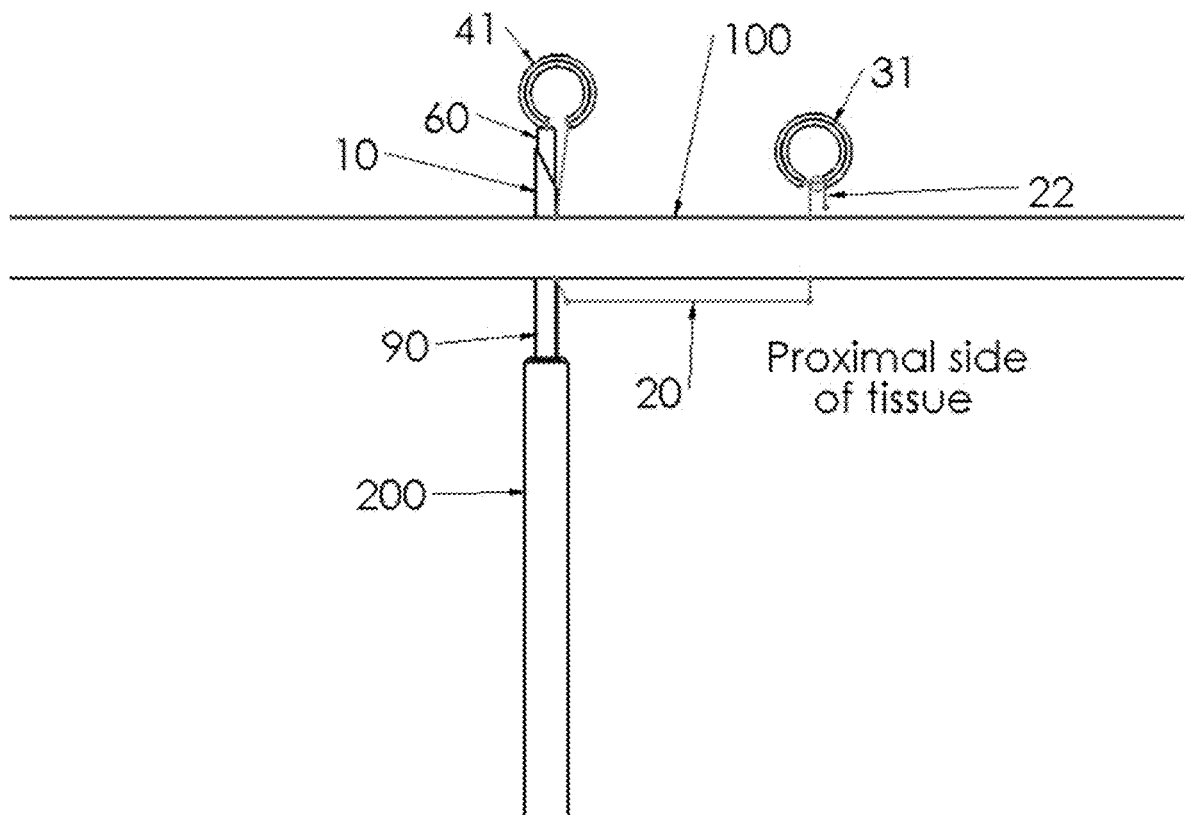
FIG. 2F shows a schematic cross section illustration of a delivery device with a second braided anchor segment after the suture has been pulled taut a second time.

FIG. 2F shows a schematic cross section illustration of a second braided anchor segment 41 after the suture 20 has been pulled taut a second time. As a result of the suture 20 being pulled taut, the second braided suture segment 40 has been deformed into a second braided anchor segment 41. The second braided anchor segment 41 is still adjacent to the first drive tube 60 after the suture 20 has been pulled taut a first time.

At this point in the deployment of the flexible braided anchor segment assembly 5, the suture 20 has been pulled taut twice. First, it was pulled taut to deform the first braided suture segment 30. Then, the suture was pulled taut a second time to deform the second braided suture segment 40.

Figure 2G:
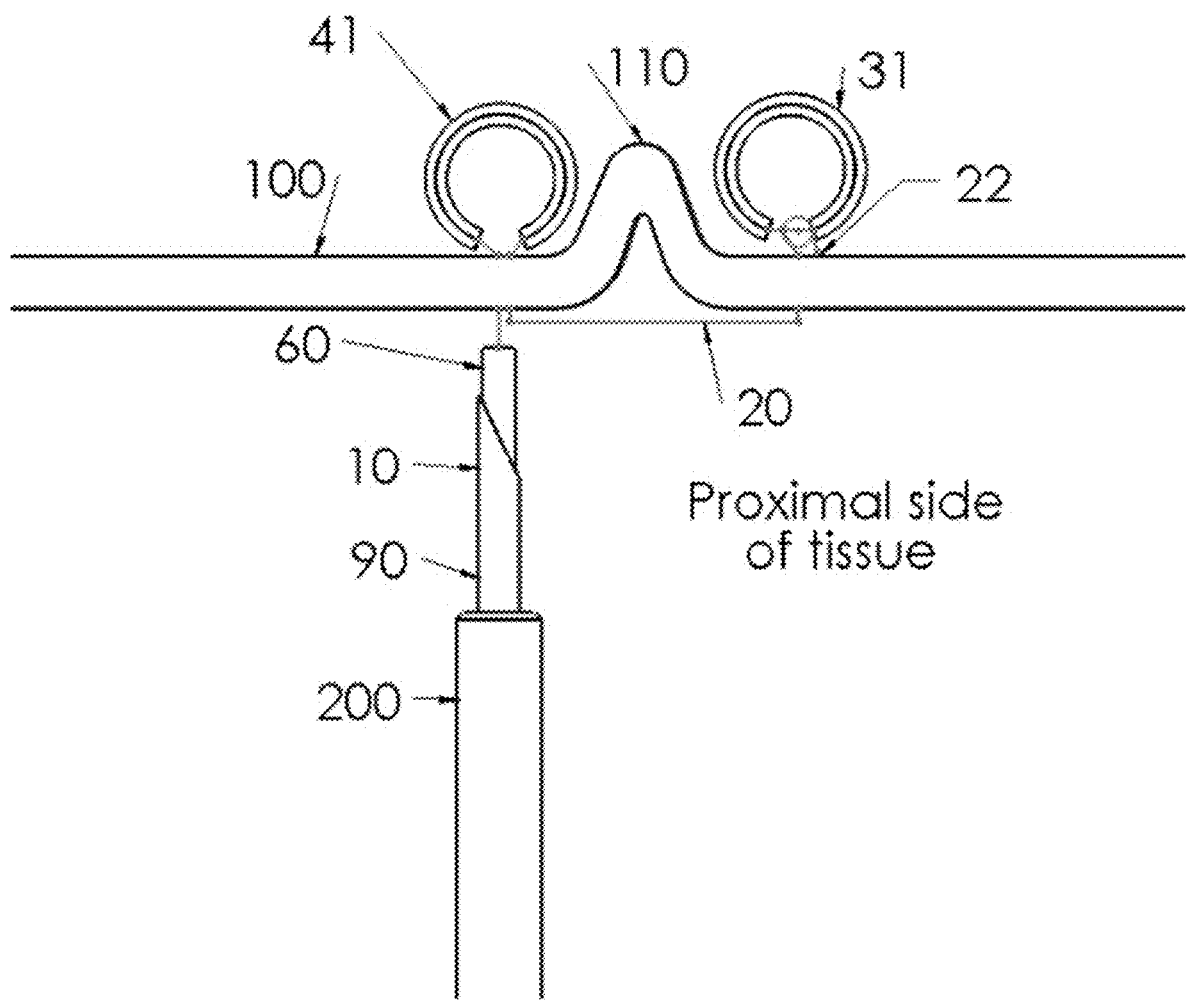
FIG. 2G shows a schematic cross section illustration of a delivery device with the first braided anchor segment and second braided anchor segment after the needle has been withdrawn from the tissue and suture has been pulled taut a third time.

FIG. 2G shows a schematic cross section illustration of the first braided anchor segment 31 and second braided anchor segment 41 after the needle 10 has been withdrawn from the tissue 100 and suture 20 has been pulled taut a third time. Braided anchor segments 31, 41 are positioned on a distal surface of a tissue 100. By pulling the suture 20 taut a third time after the needle has been removed, the third pulling of the suture 20 moves the first anchor segment 31 and the second braided anchor segment 41 together. By pulling the first two anchor segments 31,41 together, a fold 110 is formed in the tissue 100 between the first two anchor segments 31,41.

The portion of the flexible strand 20 that connects braided anchor segments 31 and 41 on the proximal surface of the tissue 100 has been pulled taut thereby causing the tissue 100 between the braided anchor segments 31 and 41 to be pulled together and to form a fold 110. The first braided anchor segment has a sliding slipknot 22 that anchors the anchor in the tissue 100. This figure illustrates braided anchor segments 31, 41 are positioned on a distal surface of a tissue 100. The braided anchor segments are interconnected via a flexible strand (e.g., a suture) 20.

Figure 2H:
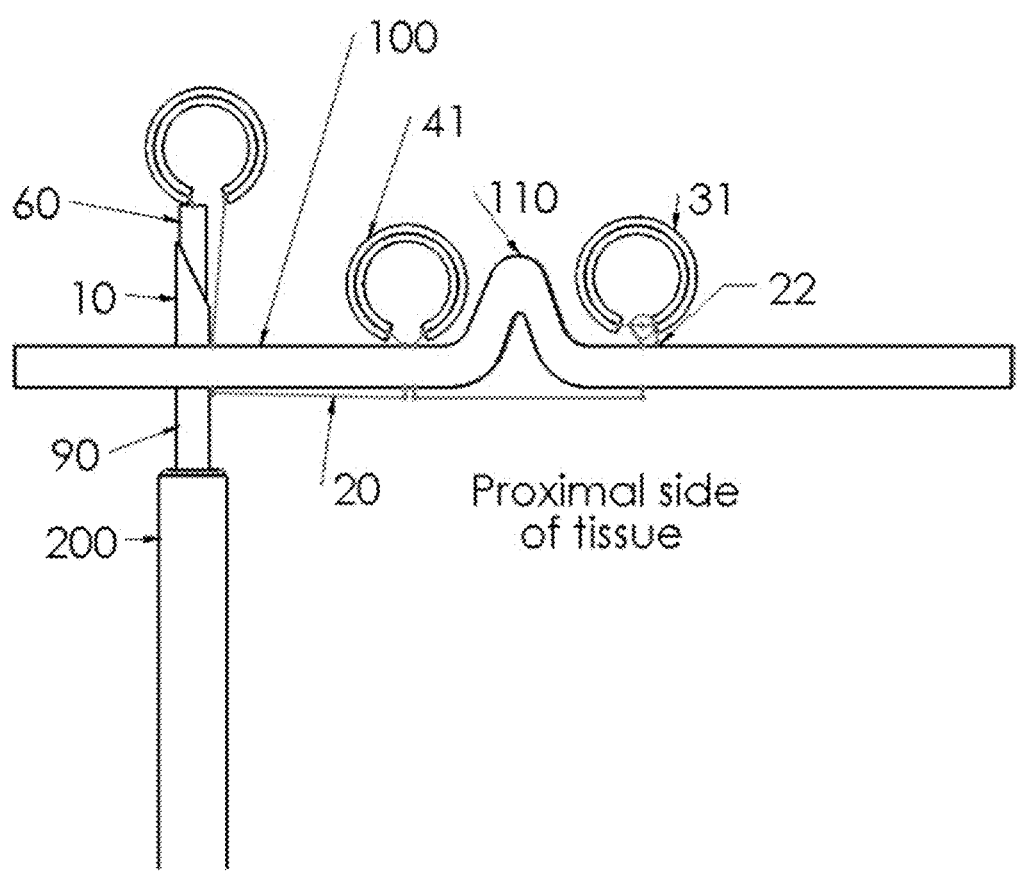
FIG. 2H shows a schematic cross section illustration of a delivery device with the first braided anchor segment, second braided anchor segment, and a third braided anchor segment.

FIG. 2H shows a schematic cross section illustration of the first braided anchor segment 31, second braided anchor segment 41, and a third braided anchor segment 51. The third braided anchor segment 51 is in a stage of being implanted in the tissue 100. The third braided anchor segment 51 is at the distal end of the delivery needle 10 and is adjacent the second drive tube 60. In FIG. 2H, the suture has been pulled taut a fourth time deforming the third braided suture segment into the third braided anchor segment 51.

Figure 3:
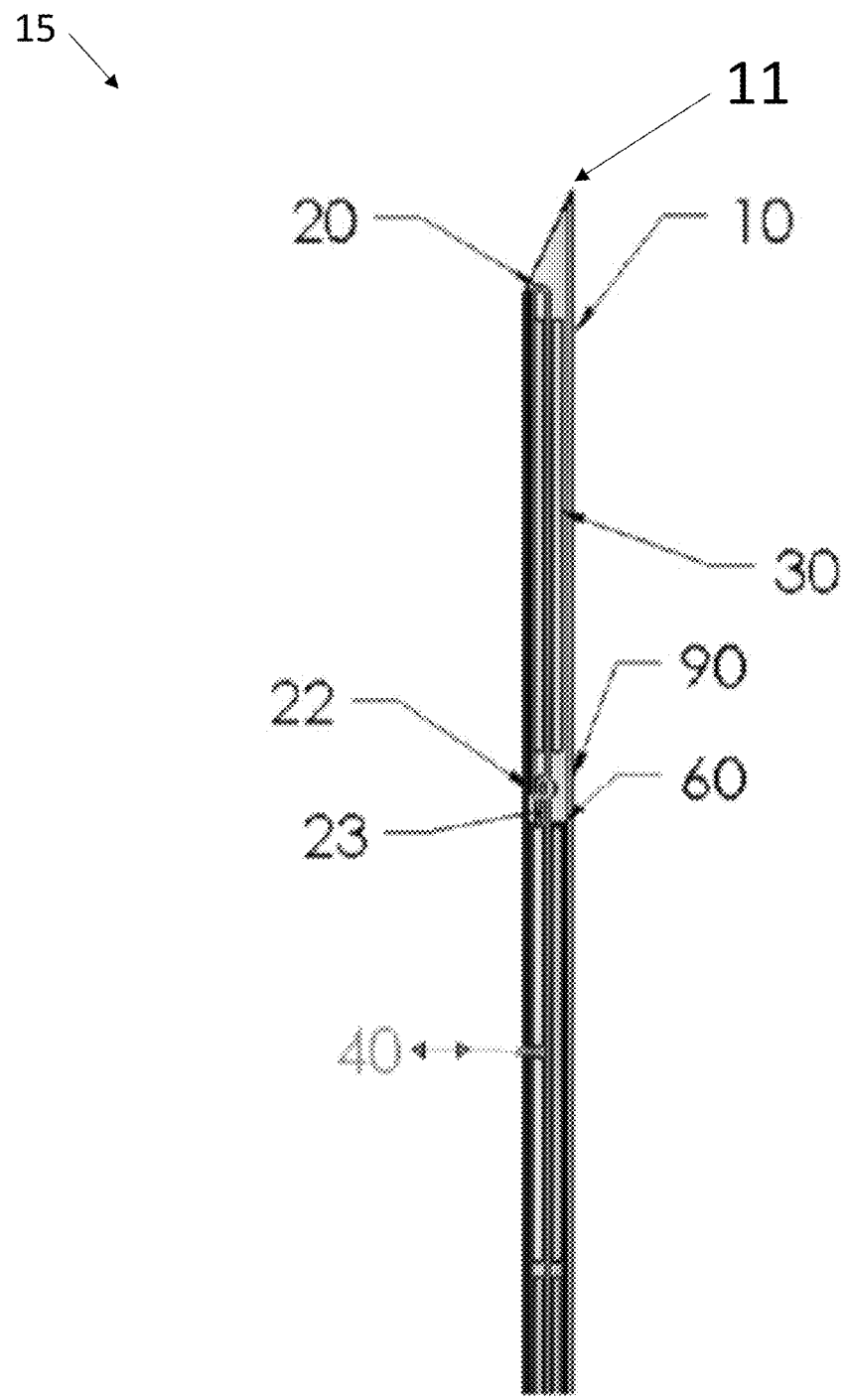
FIG. 3 is a cross section of an embodiment of a delivery device with portion of a delivery device including an outer tube having a delivery needle with a needle tip.

FIG. 3 is a cross section of an embodiment of a portion of a delivery device including an outer tube 90 having a delivery needle 10 with a needle tip 11. The outer tube 90 is preloaded with three braided suture segments 30,40,50 that are interconnected via a suture 20. The braided suture segments (e.g., segments, or suture segments) are a hollow material which enables suture 20 to pass and slide through each of the braided suture segments. The suture 20 incorporates a sliding slip knot 22 that is placed proximally to segment 30. Segment 30 is positioned to be the first suture segment to be delivered. As such, it is a primary braided suture segment, because the sliding slip knot is placed proximally to the braided suture segment 30 to allow it to participate in anchoring the primary suture segment 30 on the distal side of the tissue.

A needle tip 11 on a delivery needle 10 is used to pierce (e.g., puncture) the tissue 100 for placement of each segment. The needle tip 11 is a sharp point on the delivery needle 10. First drive tube 60 is advanced to push primary suture segment 30 out of the needle 10, and then remains in the advanced position. Suture end (e.g., suture tail) 23 is the cut end of the suture 20 after the formation of the sliding knot 22. Suture tail 23 may be used as a barb to increase holding strength or aid in preventing pullout of slip knot 22 or first braided anchor segment 31. Braided suture segment 40 is positioned in first drive tube 60.

Figure 4:
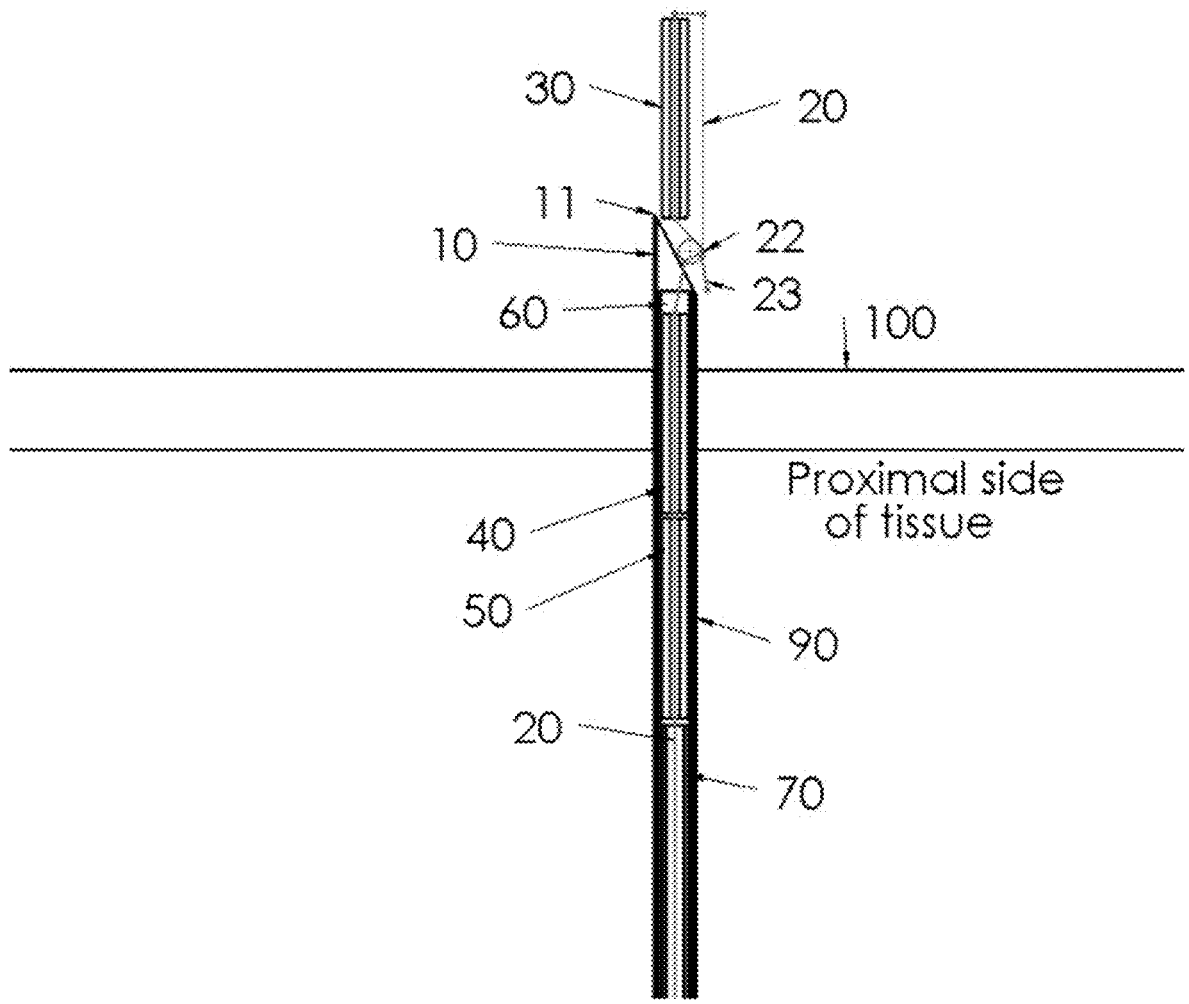
FIG. 4 is a cross section of an embodiment of a delivery device with a portion of a delivery device that has punctured the tissue and has delivered the first braided suture segment to a distal side of tissue

FIG. 4 is a cross section of an embodiment of a portion of a delivery device that has punctured the tissue 100 and has delivered the first braided suture segment 30 to a distal side of tissue 100. FIG. 4 shows needle 10 and needle tip 11 punctured through tissue 100 with segment 30 pushed out of needle 10 by first drive tube 60. After extruding segment 30 from the delivery needle 10, first drive tube 60 remains locked in the position with respect to needle tip 11. Suture segments 40 and 50 are positioned in first drive tube 60. In some embodiments, suture segments are pressure fit in first drive tube 60.

Second drive tube 70 is located in first drive tube 60 with the distal end of second drive tube 70 adjacent the proximal end to braided suture segment 50. Second drive tube 70 has an outer diameter that is smaller than the inner diameter of first drive tube 60, and second drive tube 70 is used to push the second through final suture segments out of the distal end first drive tube 60. Each braided suture segment, beginning with the second braided suture segment is extruded in order from the first drive tube 60 as the column of suture segments is pushed by second drive tube 70. The suture 20 is threaded through each suture segment. Once the distal end of each successive suture segment is extruded out of first drive tube 60, the segments exit delivery needle 10 to the distal side of tissue 100. The second and follow on segments that are extruded from the distal end of first drive tube 60 move through first drive tube 60 and outer tube 90 only in the distal direction. It is surprising that the disclosed delivery process moves in a distal direction only and does not have to retract to load subsequent anchors, nor are the braided suture segments carried on an external slider device. Furthermore, the flexible strand (e.g., suture) traverse the entire length of the bore of the delivery handle and exits the delivery handle. Additional surprising features include that the braided suture segments slide along the first drive tube 60 and are not on or related to being delivered over a rod, and that the delivery device can deploy many devices, from 1 braided suture segment up to and including 25 braided suture segments.

Figures 5A, 5B, 5C:
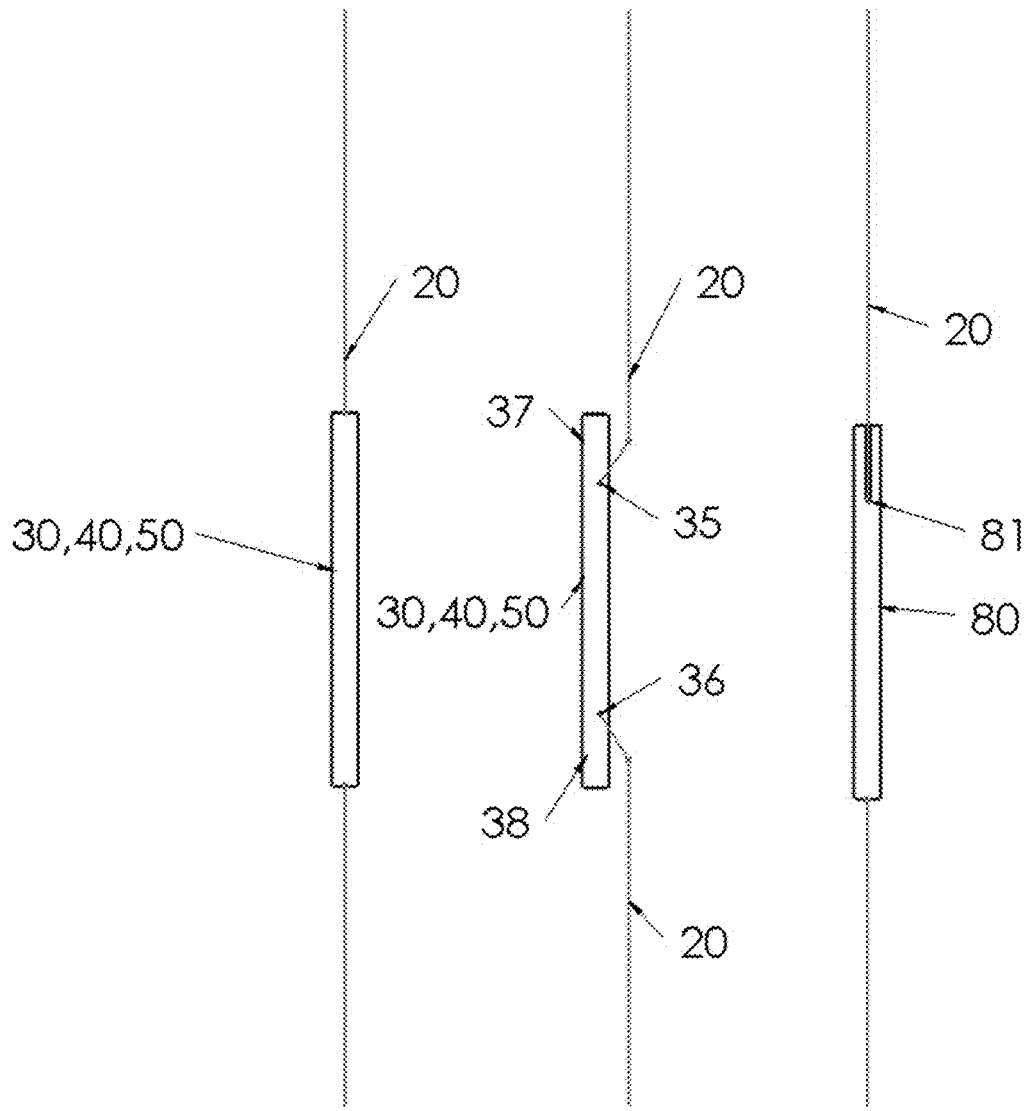
FIG. 5A shows an embodiment of a braided suture segment.
FIG. 5B shows another embodiment of a braided suture segment.
FIG. 5C shows another embodiment of a braided suture segment.

FIG. 5A shows an embodiment of a braided suture segment 30, 40, or 50 and is hollow allowing for suture 20 to pass and slide through it. In embodiments, there may be from 1 to 25 braided suture segments on a suture 20, while in some embodiments there may be 1 to 10 braided suture segments on a suture 20, while in still other embodiments there may be 1 to 5 braided suture segments on a suture 20, while in still other embodiments there may be 1 to 3 braided suture segments on a suture 20, while in still other embodiments there may be only 1 braided suture segment on a suture 20.

FIG. 5B shows an embodiment of a braided suture segment 30, 40, or 50 that has been modified such that the suture 20 is passed thru the braided fibers of the side wall of the segments 30, 40, 50, into the cannulation and back out thru the braided fiber side wall again. A feature of this version is that when the segment is placed distally past the tissue and pulled taut, the free ends 37 and 38 would aid in preventing any pullout back thru the hole created by the needle 10.

FIG. 5C shows an embodiment of a braided suture segment 80 having a slit or cut 81. The slit or cut 81 can be formed by a razor blade or any suitable cutting device and its function is to spread the cylindrical device yet further when the suture 20 is pulled taut. The suture 200 would enter the slit 81 causing the slit 81 to split apart or widen. Slits 81 can be on one or both ends of the braided suture segment.

FIG. 6A shows a schematic illustration of an embodiment of braided suture segments on a suture 20. In this embodiment, a series of suture segments are strung on a suture with a slip knot 22 being positioned after the final braided suture segment on the suture 20. FIG. 6A shows a first braided suture segment 130, a second braided suture segment 140, a third braided suture segment 150, and a fourth braided suture segment 160 on a suture 20. In this embodiment, a slip knot 22 is positioned proximal to the fourth braided suture segment 160. That is, in this embodiment, there is no slip knot present at the proximal end of the first braided anchor segment 31, but the slip knot is positioned following the final braided suture segment threaded onto the suture.

In other embodiments, a slip knot or other locking mechanism may be positioned proximally to any segments of an assembly of braided suture segments. That is, a slip knot 22 or other locking mechanism may be positioned proximal to any of suture segments 130, 140, 150, or 160, for example.

FIG. 6B shows a schematic illustration of an assembly of braided anchor segments as they are deployed on the distal side of a tissue. In this embodiment, the assembly of braided suture segments is only anchored to the tissue at where the slip knot is pulled taut. In this embodiment, the assembly of braided anchor segments has a large surface area that enables a large securing surface with only one hole formed in the tissue. This may be useful in retracting tissue from other tissue and holding it in place while other procedures are being undertaken.

FIG. 7A shows a schematic illustration of an embodiment of a long braided suture segment 170 on a suture 20. In this embodiment the long braided suture segment 170 may be between 40 mm and 70 mm. In this embodiment, a slip knot 22 is positioned proximal to the long braided suture segment 170. In this embodiment, the long braided anchor 170 segment has a large surface area that enables a large securing surface with only one hole formed in the tissue. This may be useful in retracting tissue from other tissue and holding it in place while other procedures are being undertaken.

FIG. 7B shows a schematic illustration of a long braided anchor segment 171 as it is deployed on the distal side of a tissue. In this embodiment, the long braided anchor segment 171 is only anchored to the tissue at where the slip knot is pulled taut. In this embodiment, the long braided anchor segment 171 has a large surface area that enables a large securing surface with only one hole formed in the tissue. This may be useful in retracting tissue from other tissue and holding it in place while other procedures are being undertaken.

Figure 8:
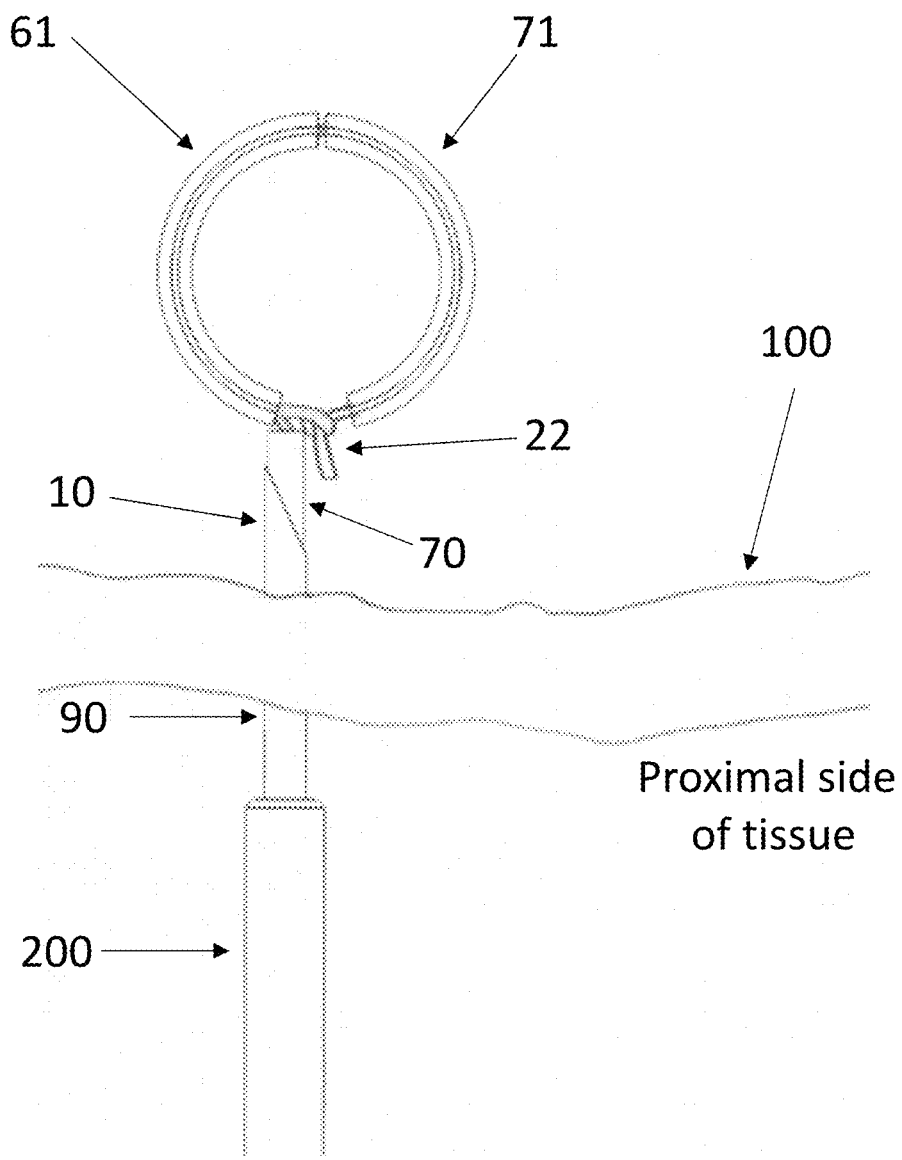
FIG. 8 shows still another embodiment of a braided suture segment.

FIG. 8 shows a schematic cross section illustration of a delivery device with two braided anchor segments 61,71 after the suture 20 has been pulled taut a first time. As a result of the suture 20 being pulled tight, the first braided anchor segment 61 and the second braided anchor segment 71 have been deformed into a dual braided anchor segment 61,71. In this embodiment, the dual braided anchor segment 61,71 has a large surface area that enables a large securing surface with only one hole formed in the tissue. This may be useful in retracting tissue from other tissue and holding it in place while other procedures are being undertaken.

Note that in this embodiment, there is no slip knot present at the proximal end of the first braided anchor segment 61. Here, the slip knot 22 is tied off proximal to braided suture segment 71.

Figure 9A:
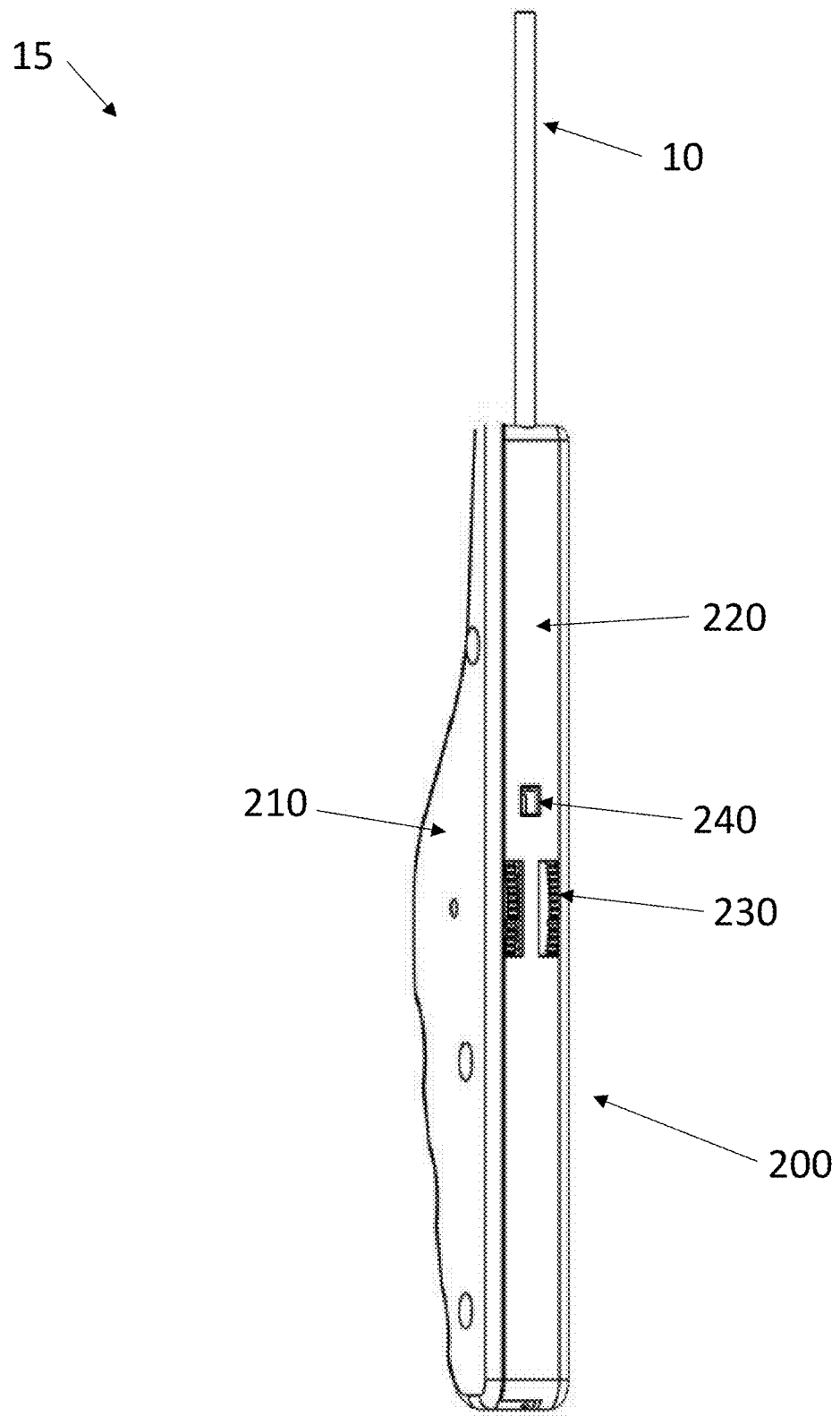
FIG. 9A shows an embodiment of a delivery device with a handle assembly with handle cover screwed to handle base.

FIG. 9A shows an embodiment of a delivery device with a handle assembly 200 with handle cover 210 screwed to handle base 220. Outer tube 90 is attached to handle base 220 with wheel 230 inside of the handle assembly 200. Rack 240 includes a visual numerical character to show the position of each braided suture segment as each braided suture segment is deployed. A needle is not shown on the outer tube 90.

Figure 9B:
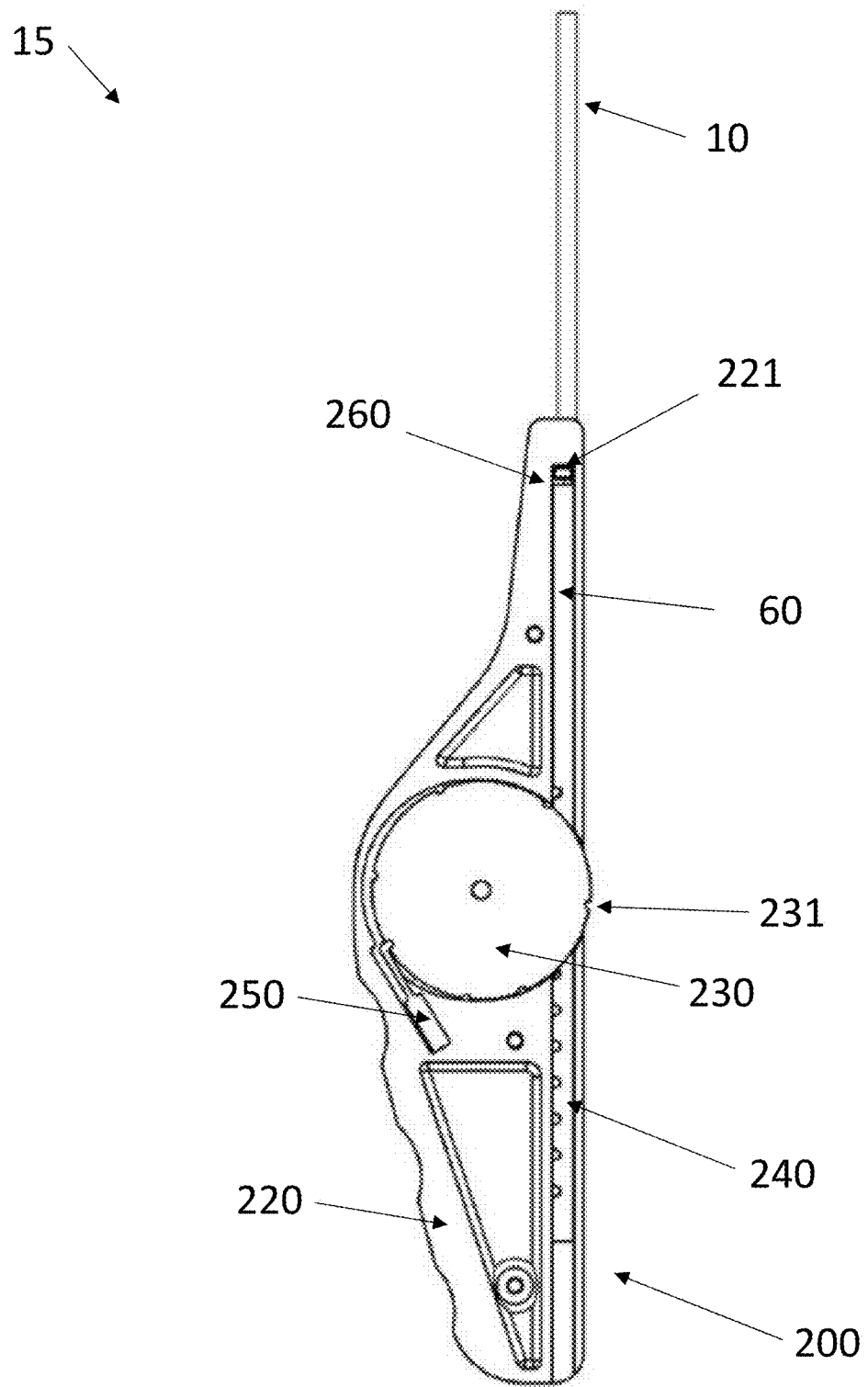
FIG. 9B shows an embodiment of a delivery device with a handle assembly with the handle cover removed for visualization.

FIG. 9B shows an embodiment of a delivery device with a handle assembly 200 with the handle cover 210 removed for visualization. Wheel 230 has an internal drive gear, not shown, that meshes with rack 240. As wheel 230 is rotated counterclockwise pawl 250 engages in the wheel cogs 231 to stop at predetermined locations. As rack 240 advances, the first drive tube 60 is advanced to extrude a first braided suture segment (e.g., segment) out of the needle (not shown). A spring (not shown) may be included in the handle assembly to drive first drive tube 60. Once the first braided suture segment is out of the needle, the first drive tube 60 is temporarily fixed to stop 260 until stop 260 engages with handle edge 221. In embodiments, a spring (not shown) may be positioned between stop 260 and handle edge 221. This will be the first position for the handle assembly. The first segment is also known as the primary segment, since once the primary segment is deployed, the primary segment 30, and first drive tube 60 will disengage from rack 240 via a dimple or breakaway. First drive tube 60 will now stay in this fixed position against handle stop 221.

Subsequent deployment of additional braided suture segments will be accomplished with a second drive tube (not shown). The second drive tube is positioned within first drive tube 60 and attached to rack 240, and will drive through first drive tube 60 as wheel 230 is rotated to a different positional cog 231 with pawl 250. This can be repeated for additional fixation devices.

Figure 10:
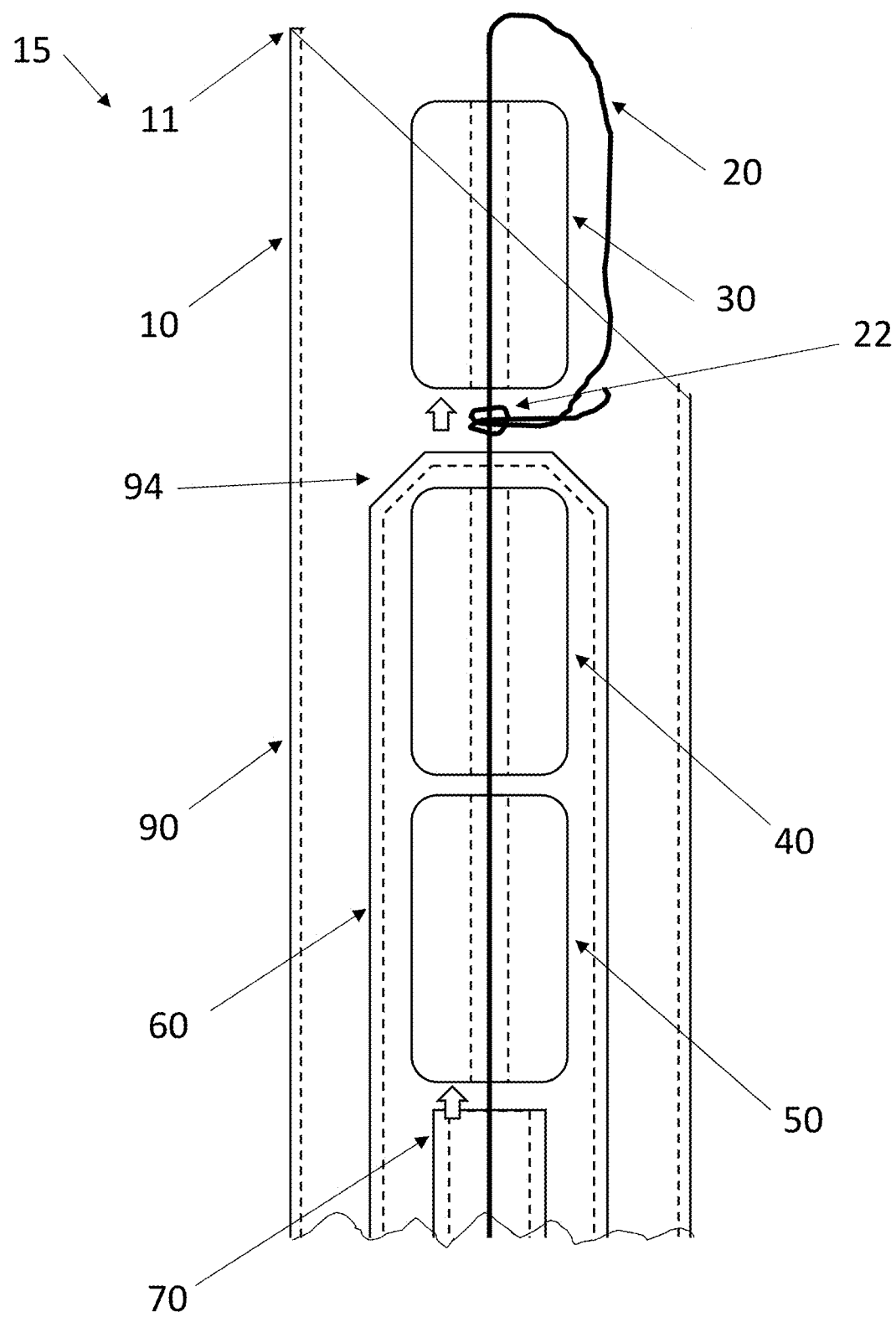
FIG. 10 shows a schematic cross section of an embodiment of a delivery device.

FIG. 10 shows a schematic cross section of an embodiment of a delivery device 15. An outer tube 90 has a delivery needle 10 and a needle tip 11. A first drive tube 60 is positioned concentrically inside of the outer tube 90. First drive tube 60 an outer diameter that is smaller than the inner diameter of outer tube 90, and first drive tube 60 is used to push first braided suture segment 30 out of the distal end outer tube 90 through the delivery needle 10. In embodiments, a distal end of the first drive tube 60 may include a detent 94 that may provide friction so that there is a slight resistive force to the extrusion of braided suture segments. Once the first drive tube 60 has extruded the first suture segment 30, the first drive tube 60 may become temporarily fixed in the outer tube 90.

Each braided suture segment, beginning with the second braided suture segment 40 is extruded in order from the first drive tube 60 as the column of suture segments is pushed by second drive tube 70. A second braided segment 40 and a third braided segment 50 are positioned in the first drive tube 60. In embodiments, the number of braided suture segments positioned in the first drive tube 60 may be between 1 and 10, and in some embodiments, the number of braided suture segments positioned in the first drive tube 60 may be between 2 and 5. A second braided suture segment 40 through a final suture segment may be preloaded in a first drive tube 60 prior to initiation of a tissue anchoring procedure.

A suture (e.g., flexible strand) may be threaded through the braided suture segments and looped around the first suture segment 30 and tied into a slip knot 22 around the suture 20 between the proximal end of the first braided suture segment 30 and the distal end of the first drive tube 60.

A second drive tube 70 is positioned concentrically in the first drive tube 60 with its distal end proximal to the third braided suture segment 50 (e.g., the last braided suture segment that is preloaded into the first drive tube 60). Second drive tube 70 has an outer diameter that is smaller than the inner diameter of first drive tube 60, and second drive tube 70 is used to push the second through final suture segments out of the distal end first drive tube 60. Each braided suture segment, beginning with the second braided suture segment is extruded in order from the first drive tube 60 as the column of suture segments is pushed distally by second drive tube 70. In general, the second drive tube 70 is positioned proximal to the last braided suture segment in the first drive tube 60 regardless of the number of braided suture segments preloaded into the first drive tube 60.

In some embodiments, a delivery device may not include a first drive tube 60 (not shown). In embodiments, the braided suture segments 30,40,50 may be preloaded into an outer tube 90, and extruded by pushing the braided suture segments 30,40,50 out of outer tube 90 with the second drive tube 70. The braided suture segments 30,40,50 may be press fit into the outer tube 90 to provide friction to the sliding of the braided suture segments 30,40,50 against the pressure applied by the second drive tube 70.

Figure 11:
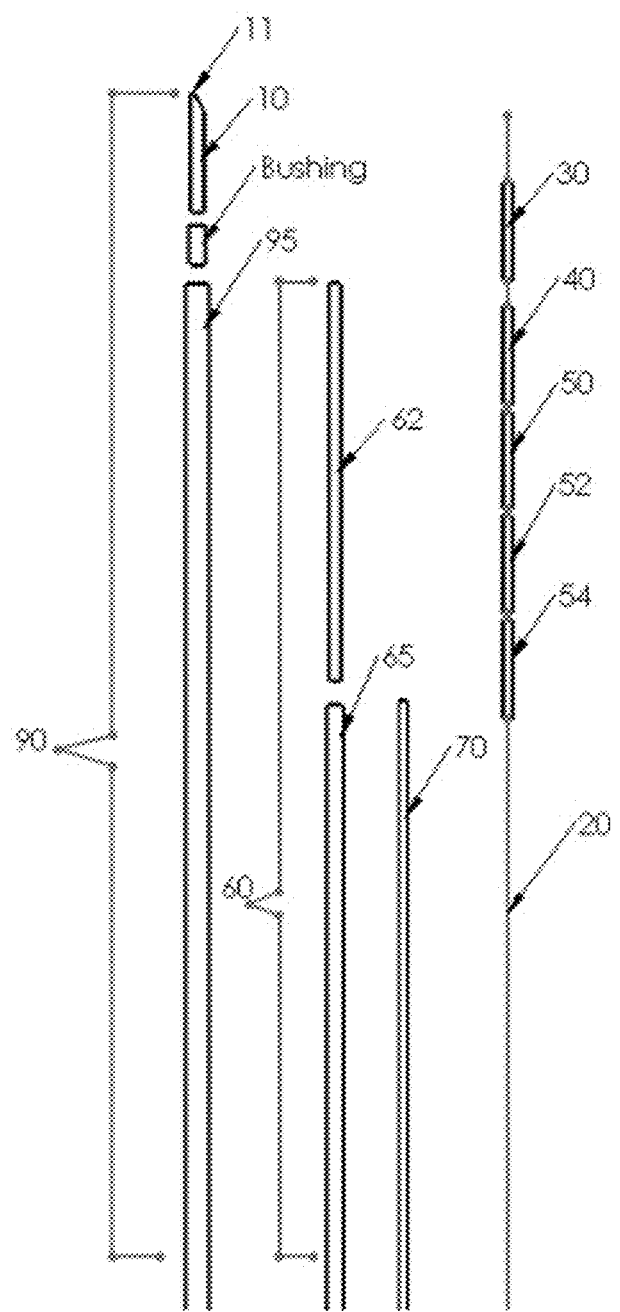
FIG. 11 shows embodiments of a delivery device with an outer tube, a first drive tube, a second drive tube, and an assembly of braided suture segments strung on a flexible filament.

FIG. 11 shows embodiments of an outer tube 90, a first drive tube 60, a second drive tube 70, and an assembly of braided suture segments strung on a flexible filament (e.g., suture) 20.

In some embodiments, the outer tube 90 is a single tube that includes a base outer tube 95, and a needle 10 having a needle point 11. In some embodiments, the single tube of the outer tube 90, may or may not have a bushing included. In some embodiments, the outer tube 90 may comprise a two-piece tube having a base outer tube 95 coupled with a needle 10. In some embodiments, the outer tube 90 may comprise a three-piece tube having the base outer tube 95 coupled with a bushing and the needle 10. In embodiments when the outer tube 90 comprises more than 1 part, the various parts may be fabricated from different rigid materials. In other embodiments when the outer tube 90 comprises more than 1 part, the various parts may be fabricated from similar rigid materials.

FIG. 11 also shows embodiments of the first drive tube 60. In some embodiments, the first drive tube 60 is a single tube. In some embodiments, the first drive tube 60 may comprise a two-piece tube having a base first drive tube 65, and a first drive tube tip 62. In embodiments when the first drive tube 60 comprises more than 1 part, the various parts may be fabricated from different rigid materials. In other embodiments when the first drive tube 60 comprises more than 1 part, the various parts may be fabricated from similar rigid materials.

FIG. 11 further shows embodiments of the second drive tube 70. The second drive tube 70 is made from rigid materials. The rigid materials may include one or more rigid materials, such as a steel, aluminum, titanium, and so on. The rigid material may also include metallic alloys such as nitinol.

FIG. 11 still further shows embodiments of the an assembly of five braided suture segments 30,40,50,52,54 with a flexible filament (e.g., suture) 20 threaded through bore holes that go through a length-wise dimension of the braided suture segments.

Figure 12:
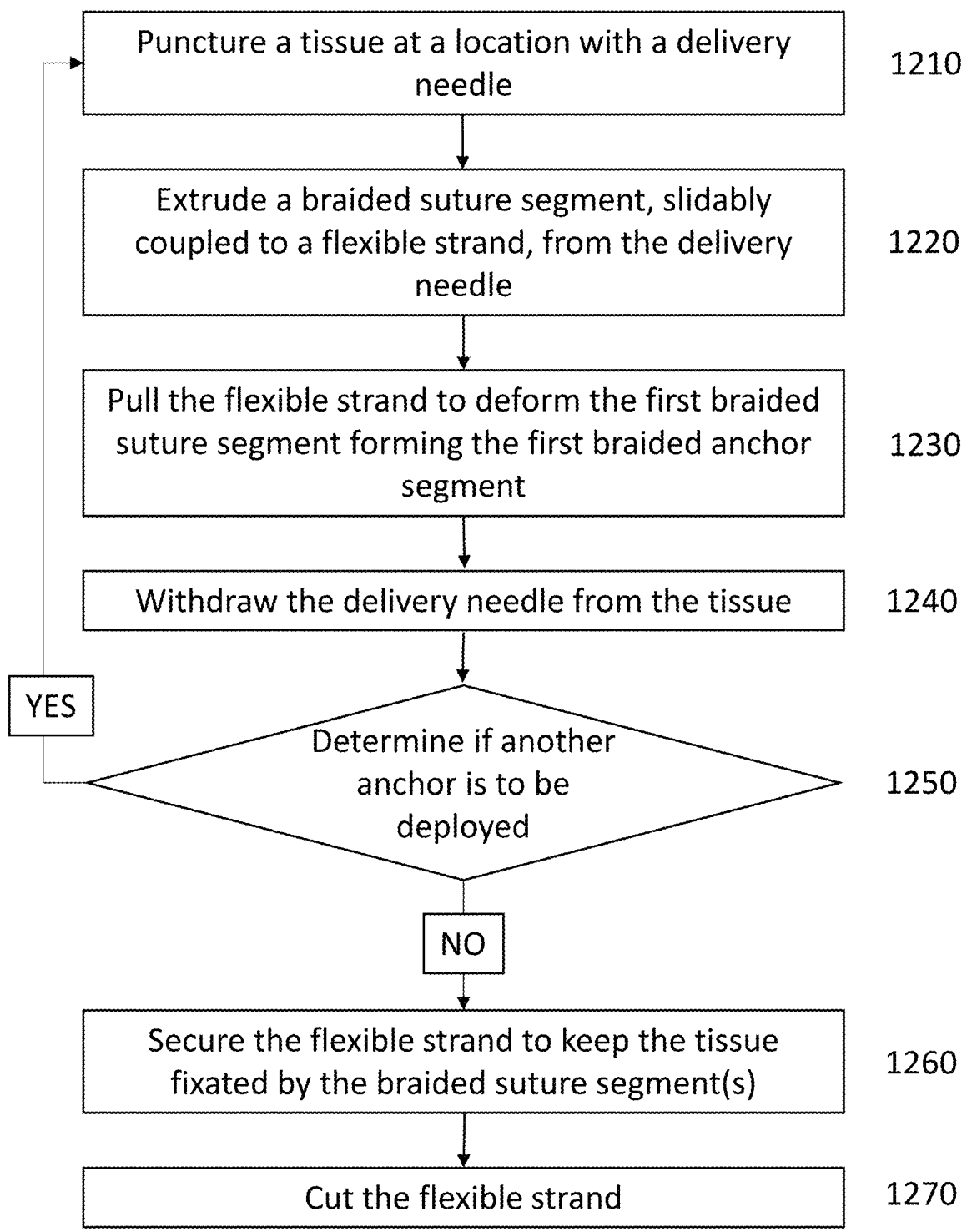
FIG. 12 shows steps of an embodiment of a method for implanting braided anchor segments connected via a single flexible strand for tissue fixation.

FIG. 12 shows steps of an embodiment of a method for implanting braided anchor segments connected via a single flexible strand (e.g., suture) for tissue fixation.

At 1210, puncture a tissue at a location with a delivery needle. The needle having a needle tip punctures the tissue from a proximal side of the tissue to a distal side of the tissue. The needle is at a distal end of an outer tube, and the outer tube is coupled to a handle assembly.

At 1220, extrude a braided suture segment, slidably coupled to a flexible strand, from the delivery needle. The braided suture segment is extruded from the needle on the distal side of the tissue. The braided suture segment is pushout distally out of the needle by a first drive tube.

At 1230, pull the flexible strand to deform the braided suture segment forming the braided anchor segment. As a result of the flexible strand being pulled tight, the first braided suture segment is deformed into a first braided anchor segment.

At 1240, withdraw the delivery needle from the tissue. The delivery needle is withdrawn from the tissue leaving behind the braided anchor segment on the distal side of the tissue.

At 1250, determine if another anchor is to be deployed. A determination is made as to whether an additional braided anchor segment is required to fixate the tissue. If it is determined that an additional braided anchor segment is necessary to fixate the tissue, then the method returns to step 1210 to initiate placing an additional braided anchor segment on the distal side of the tissue. If it is determined that an additional braided anchor segment is not necessary to fixate the tissue, then the method advances to step 1260 to secure the flexible strand.

At 1260, secure the flexible strand to keep the tissue fixated by the braided suture segment(s). The flexible strand (e.g., suture) is secured by engaging a locking mechanism (e.g., cinch) with the suture to lock the suture and prevent the fixated tissue from pulling apart. By tightening the suture to draw in the anchors and close the opening in the tissue, the flexible assembly braided anchor segments has closed the opening like pulling purse strings to close a purse.

At 1270, cut the suture. The flexible strand is cut on the distal side of the locking mechanism after the flexible strand has been pulled taut and secured by the locking mechanism.

The embodiments of the invention described above are intended to be merely exemplary; numerous variations and modifications will be apparent to those skilled in the art. Such variations and modifications are intended to be within the scope of the present invention as defined by any of the appended claims.

What is claimed is:

1. A method for implanting a plurality of braided suture segments connected via a single flexible strand for tissue fixation, comprising;
   puncturing the tissue at a first location with a delivery needle;
   extruding a first braided suture segment from the delivery needle, the first braided suture segment is the first of a plurality of braided suture segments slidably coupled to a flexible strand, the flexible strand being threaded through a bore hole in the first braided suture segment;
   pulling the flexible strand a first time to deform the first braided suture segment forming the first braided anchor segment, pulling the flexible strand the first time tightens a slipknot around a proximal end of the first braided suture segment, tightening the slipknot is configured to anchor the first braided anchor segment to the tissue to prevent the first braided anchor segment from pulling through the tissue;
   withdrawing the delivery needle from the tissue a first time;
   puncturing the tissue at a second location with the delivery needle;
   extruding a second braided suture segment from the delivery needle;
   pulling the suture a second time to deform the second braided suture segment forming the second braided anchor segment;
   withdrawing the delivery needle from the tissue a second time;
   pulling the suture a third time, the pulled suture causing the second anchor segment to be moved toward the first braided anchor segment;
   securing the suture to keep the tissue fixated by the plurality of braided suture segments; and
   cutting the suture, the suture is cut a distance away from the proximal end of a final braided anchor segment of the plurality of the braided anchor segments.

2. The method of claim 1, following pulling the suture a third time, and before securing the suture, further comprising:
   puncturing the tissue at a third location with the delivery needle;
   extruding a third braided suture segment from the delivery needle;
   pulling the suture a fourth time to deform the third braided suture segment forming the third braided anchor segment;
   withdrawing the delivery needle from the tissue a third time; and
   pulling the suture a fourth time, the pulled suture causing the third braided anchor segment to be moved toward the second braided anchor segment.

3. The method of claim 1, wherein:
   the first braided suture segment is a primary first braided suture segment;
   the extruding the first braided suture segment is accomplished by advancing first drive tube to push the first braided suture segment out of the delivery needle; and
   after advancing first drive tube to push the first braided suture segment out of the delivery needle, first drive tube remains in an advanced position temporarily.

4. The method of claim 1, wherein the extruding a second braided suture segment is accomplished by advancing second drive tube to push the second braided suture segment out of the delivery needle.

5. The method of claim 1, wherein the second location is between about 5 mm and about 15 mm from the first location.

6. The method of claim 1, wherein the securing the suture comprises a locking device or an overhead knot that can be run down to a fixation site.

7. The method of claim 1, wherein the securing the suture comprises locking the suture in place using a locking mechanism comprising at least one of a tag, a barb, a cinch, a toggled needle, or a distel knot.

8. A surgical device for implanting a flexible braided anchor assembly for tissue fixation, comprising:
   a handle assembly, the handle assembly having a cylindrical bore passing through the handle assembly on a center axis along a length of the handle assembly;
   an outer tube positioned in the cylindrical bore of the handle assembly, the outer tube being hollow and having a common center line with the cylindrical bore of the handle assembly, the outer tube comprising a delivery needle having a needle tip at a distal end of the outer tube;
   a plurality of braided suture segments slidably coupled to a flexible strand, the flexible strand being translationally threaded through plurality of braided suture segments;
   a first drive tube positioned in the outer tube and having a common center line with the outer tube, the first drive tube configured to extrude a first braided suture segment; and
   a second drive tube positioned in the first drive tube and having a common center line with the first drive tube, the second drive tube configured to extrude remaining braided suture segments of the plurality of braided suture segments, wherein the remaining braided suture segments of the plurality of braided suture segments are translationally threaded through and pressure fit within the first drive tube.

9. The surgical device of claim 8, wherein each of plurality of braided suture segments comprises a hollow braided suture segment.

10. The surgical device of claim 8, wherein:
    the suture comprises a monofilament strand; and
    the plurality of braided suture segments comprises a plurality of hollow braided suture segments aligned end to end having the monofilament strand threaded through the aligned plurality of hollow braided suture segments.

11. The surgical device of claim 8, wherein a column strength of the plurality of hollow braided suture segments is increased by application of at least one of heat and a cyanoacrylate coating to each of the segments of the plurality of hollow braided suture segments.

12. The surgical device of claim 11, wherein a distal end of the flexible strand threaded through the first braided suture segment is looped around the first braided suture segment and knotted around the flexible strand between the first braided suture segment and the first drive tube.

13. The surgical device of claim 8, wherein a braided suture segment of the plurality of braided suture segments has a length of between about 5 mm and about 50 mm.

14. The surgical device of claim 9, wherein each of the braided suture segments of the plurality of braided suture segments has a length of between about 5 mm and about 12 mm.

15. The surgical device of claim 8, wherein each of the plurality of braided suture segments is treated to increase a rigidity of the plurality of braided suture segments slidably coupled to the flexible strand.

16. The surgical device of claim 15, wherein the treatment comprises:
heating each of the plurality of braided suture segments; or
applying a cyanoacrylate coating to each of the plurality of braided suture segments.

* * * * *